United States Patent [19]

Vyas et al.

[11] Patent Number: 4,853,467

[45] Date of Patent: Aug. 1, 1989

[54] NITROGEN CONTAINING DERIVATIVES OF EPIPODOPHYLLOTOXIN GLUCOSIDES

[75] Inventors: Dolatrai M. Vyas, Madison; Mark G. Saulnier, Middletown; John F. Kadow, New Haven, all of Conn.

[73] Assignee: Bristol-Myers Company, New York, N.Y.

[21] Appl. No.: 51,434

[22] Filed: May 19, 1987

[51] Int. Cl.[4] .............................................. C07H 15/26
[52] U.S. Cl. ................................... 536/17.9; 536/4.1; 536/18.1
[58] Field of Search ............................. 536/18.1, 17.9

[56] References Cited

U.S. PATENT DOCUMENTS 3,524,844  8/1970  Keller-Juslen et al. ............ 536/18.1
4,609,644  9/1986  Nemec ................................ 536/18.1

OTHER PUBLICATIONS

Holthuis, J. J. M. et al., J. Electroanal. Chem. Interfacial Electrochem., 1985, 184(2):317-29).

Ayres and Lim, Cancer Chemother Pharmacol, 1982, 7:99-101.

Primary Examiner—Johnnie R. Brown
Assistant Examiner—Elli Peselev
Attorney, Agent, or Firm—Mollie M. Yang

[57] ABSTRACT

There are provided novel nitrogen containing derivatives of epipodophyllotoxin glucoside derivatives. The novel compounds of the present invention are useful as tumor inhibiting agents.

59 Claims, No Drawings

NITROGEN CONTAINING DERIVATIVES OF EPIPODOPHYLLOTOXIN GLUCOSIDES

BACKGROUND OF THE INVENTION

1. Field of the Invention

The present invention relates to novel nitrogen containing derivatives of epipodophyllotoxin glucoside derivatives, to their therapeutic anti-tumor use, and to pharmaceutical dosage forms containing these new agents.

2. Description of the Related Art

Etoposide (VP-16, Ia) and teniposide (VM-26, Ib) are clinically useful anticancer agents derived from the naturally occurring lignan, podophyllotoxin (II). The numbering system used for nomenclature purposes is shown in Formula II. Etoposide and teniposide are epipodophyllotoxin

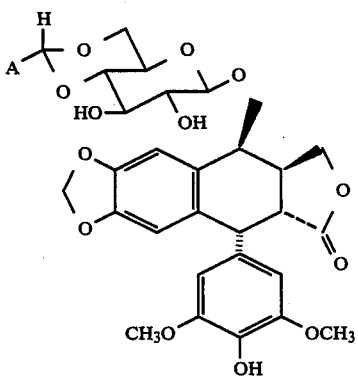

Ia A = $CH_3$

Ib A = 2-thienyl

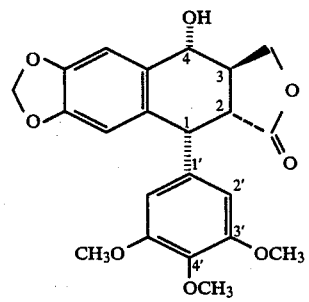

derivatives; epipodophyllotoxin being the epimer of podophyllotoxin at the 4-position. Etoposide and teniposide are active in the treatment of a variety of cancers including small cell lung cancer, non-lymphocytic leukemia, and non-seminomatous testicular cancer (AMA Drug Evaluation, 5th Edition, American Medical Association, 1983, Chicago, Illinois, p. 1554–5).

Etoposide and teniposide, and methods for producing them, are disclosed in U.S. Pat. No. 3,524,844 to Keller-Juslen et al. Etoposide 3',4'-quinone (IIIa) has been generated from electrochemical oxidation of etoposide (Holthuis J. J. M., et al, *J. Electroanal. Chem. Interfacial Electrochem.*, 1985, 184(2):317–29). The preparation of the quinone III by chemical oxidation is disclosed in U.S. Pat. No. 4,609,644 to Josef Nemec. Epipodophyllotoxin 3',4'-quinone derivatives III wherein A and Y have the definition given hereinbelow for Formula IV serve as the starting material for our preparation of the nitrogen containing epipodophyllotoxin derivatives of the present invention.

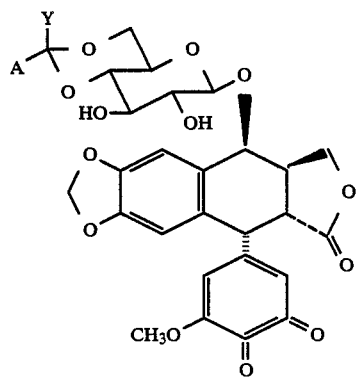

IIIa A = $CH_3$; Y = H

Ayres and Lim in Cancer Chemother Pharmacol, 1982, 7:99–101 discloses the podophyllotoxin having the formula

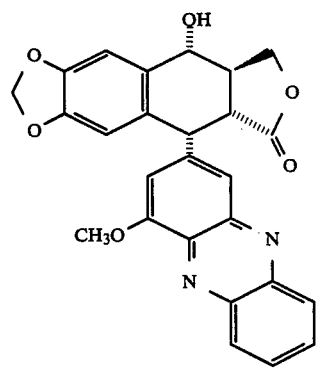

SUMMARY OF THE INVENTION

The present invention relates to antitumor compounds having the formula

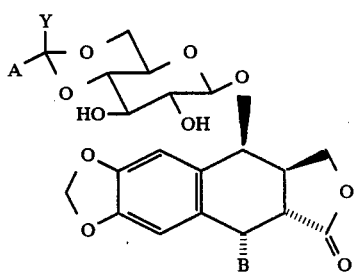

wherein
Y is H and A is selected from the group consisting of ($C_{1-10}$)alkyl; ($C_{2-20}$)alkenyl; ($C_{5-6}$)cycloalkyl; 2-furyl; 2-thienyl; aryl, aralkyl, and aralkenyl, each of the aromatic rings may be unsubstituted or substituted with one or more groups selected from halo ($C_{1-8}$)alkyl, ($C_{1-8}$)alkoxy, hydroxy, nitro, and amino; or
A and Y are each ($C_{1-8}$)alkyl; or
A and Y and the carbon to which they are attached join to form a $C_{5-6}$ cycloalkyl group; and
B is selected from the group consisting of

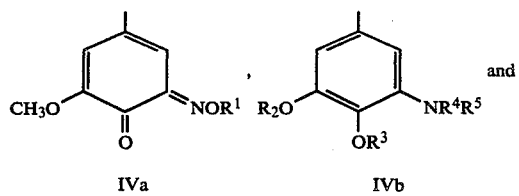

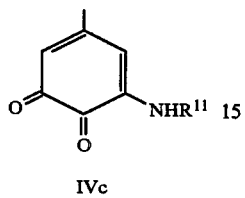

wherein
$R^1$ is $(C_{1-10})$alkyl, $(C_{4-7})$cycloalkyl, $(C_{2-10})$alkenyl, $(C_{2-10})$alkynyl, each of the above groups may be unsubstituted or substituted with one or more Z; aryl, heteroaryl, aralkyl, or heteroaralkyl, the ring portion of the above groups may be unsubstituted or substituted with one or more groups selected from $(C_{1-8})$alkyl and Z; wherein said Z is selected from halo, $(C_{1-5})$alkoxy, amino, nitro, cyano, hydroxy, and mercapto;
$R^2$ is H or methyl;
$R^{11}$ is H,

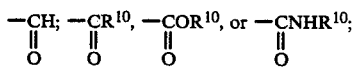

wherein $R^{10}$ is $(C_{1-10})$alkyl unsubstituted or substituted with one or more Z, or aryl$(C_{1-5})$alkyl;
$R^3$ is H or a phenol protecting group;
$R^4$, $R^5$ are each independently $R^{11}$ or $R^1$; or
$R^4$ is H and $R^5$ is sulfonyl; or

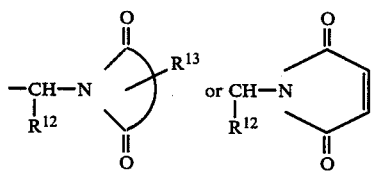

wherein $R^{12}$ is H or $(C_{1-8})$alkyl; $R^{13}$ is H, $R^1$, or $-S-R^1$; or
$R^3$, $R^4$ and $R^5$ together is

wherein $R^{14}$ is H or $(C_{1-5})$alkyl; or
$NR^4R^5$ is nitro, azido; or $N_2^{30}X^-$ with the proviso that $R^3$ is not H, wherein $X^{31}$ is an anionic group; or
$NR^4R^5$ is $N=CHR^6$, $N=CHNR^7R^8$, $N=NNHR^9$, wherein $R^6$ is as defined for $R^1$; $R^7$ and $R^8$ are each independently H or $(C_{1-8})$alkyl; $R^9$ is $(C_{1-8})$alkyl; or
$R^3$ and $NR^4R^5$ together represent diazonium hydroxide inner salt.

A preferred embodiment is wherein Y is H and A is methyl or 2-thienyl, with methyl being the most preferred.

As used herein in the specification and the claims, unless otherwise specified, $NR^4R^5$ means $R^4$, $R^5$, and the nitrogen atom they are attached to taken together. Alkyl means straight or branched saturated carbon chain such as methyl, ethyl, n-propyl, and isopropyl. Acyl means an organic residue containing the C=O radical which encompasses, but is not limited to, formyl, alkanoyl or substituted alkanoyl, arylcarbonyl, alkoxycarbonyl or substituted alkoxycarbonyl, and (ara)alkylaminocarbonyl or substituted (ara)alkylaminocarbonyl. Sulfonyl means an organic residue containing the $-SO_2-$ radical. Halo means fluorine, chlorine, bromine, or iodine. Heteroaryl means an aromatic ring having at least one non-carbon ring atom; examples include pyridine, pyrrole, thiophene, and furan.

Another aspect of the present invention provides a pharmaceutical composition comprising an antitumor compound of Formula IV and a pharmaceutically acceptable, non-toxic carrier.

A further aspect of the present invention provides a method for inhibiting tumor in a mammal comprising administering to said tumor-bearing mammal an effective amount of an antitumor compound of Formula IV.

DETAILED DESCRIPTION OF THE INVENTION

The starting material for the present invention, the ortho-quinone III may be prepared by reacting an oxidizing agent with a 4'-demethylepipodophyllotoxin-β-D-glucoside derivative I. The method is described in U.S. Pat. No. 4,609,644 which is hereby incorporated by reference.

According to one aspect of the present invention, there are provided compounds of Formula IVa

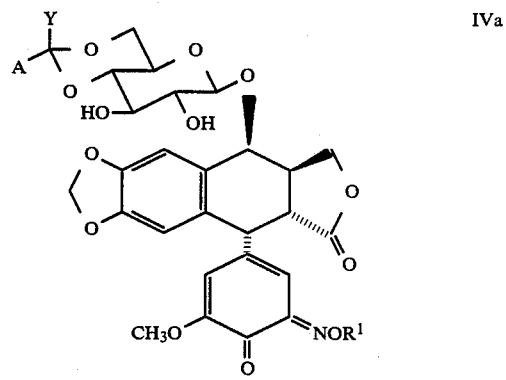

wherein A, Y, and $R^1$ are as previously defined.

A preferred embodiment provides compounds of Formula IVa wherein $R^1$ is $(C_{1-10})$alkyl, phenyl, phenyl$(C_{1-10})$alkyl, or ring substituted phenyl$(C_{1-10})$alkyl.

The 3'-oxime ethers having the Formula IVa may be obtained when the corresponding ortho-quinone of Formula III are reacted with an O-substituted hydroxylamine, or an acid addition salt thereof, in a suitable organic solvent such as pyridine. The reaction is preferably carried out at room temperature for a period sufficient to obtain the mono oxime ether, for example from about 30 minutes to about one hour. The products thus formed may be isolated and purified e.g. by flash chromatography; or alternatively, they may be reduced directly, without first being isolated, to the corresponding amine compound of Formula V.

According to another aspect of the present invention, there are provided compounds of the Formula V

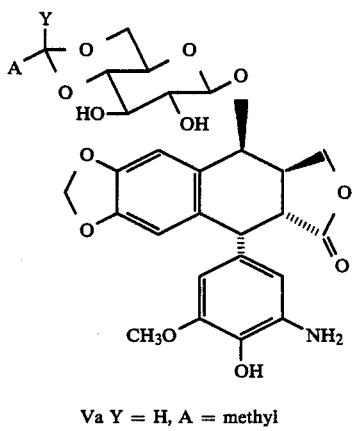

Va Y = H, A = methyl wherein A and Y are as previously defined.

The amine of Formula V may be prepared by reduction of the oxime ether of Formula IVa; and as mentioned above, either a purified compound of Formula IVa or the crude product may be used. Reduction of the oxime ether may be effected by conventional methodologies, e.g. a mild chemical reducing agent, or hydrogenation in the presence of a suitable catalyst such as Pt, Pd, Ni, Ru or Rh. Catalytic hydrogenation is preferably employed. Amine compounds of Formula V may also be prepared directly from the ortho-quinone III by treatment with ammonia or an alkylamine at room temperature; reaction with the latter yields both the amine V and the corresponding alkyl substituted amine. The preferred preparative method is the reduction of the oxime ether of Formula IVa.

The amino compounds of Formula V can react with a variety of reagents to provide compounds of the formula IVb ($R^2$ is methyl, and $R^4$ and $R^5$ are not both H). The reactions are generally carried out in inert organic solvents such as tetrahydrofuran, dichloromethane, or chloroform, under conditions that are appropriate for achieving the desired products. Products may be isolated and purified using known methods such as recrystallization and various chromatographic techniques.

Thus, another aspect of the present invention provides compounds of the Formula VI

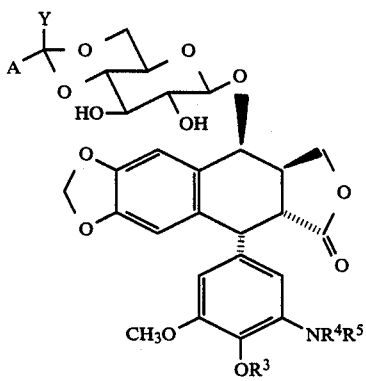

wherein A, Y and $R^3$ are previously defined; $R^4$ is H and $R^5$ is sulfonyl;

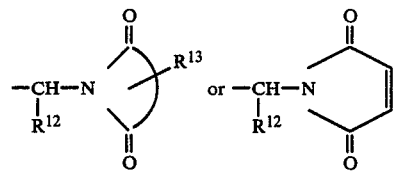

wherein $R^{10}$ is ($C_{1-10}$)alkyl unsubstituted or substituted with one or more Z, or ara($C_{1-10}$)alkyl; or $$-\underset{\underset{O}{\|}}{CH;} \ -\underset{\underset{O}{\|}}{CR^{10},} \ -\underset{\underset{O}{\|}}{COR^{10},} \ -\underset{\underset{O}{\|}}{CNHR^{10};}$$

wherein $R^{12}$ and $R^{13}$ are as previously defined.

A preferred embodiment provides compounds of Formula VI wherein $R^3$ is H.

Various acyl compunds of Formula VI may be prepared using standard procedures. To exemplify, amide derivatives may be prepared by acylating the 3'-amino group of compound V with a carboxylic acid, preferably in the presence of a condensing agent such as dicyclohexylcarbodiimide (DCC); an acid halide; or a symmetrical or unsymmetrical anhydride; or a reactive ester or amide. In a fashion analogous to the preparation of amides, sulfonamides may be prepared by reacting compounds of Formula V with a sulfonic acid derivative such as a sulfonyl halide. In general, in preparing amide derivatives using an acid halide or an anhydride, or in preparing the sulfonamide derivatives, the reactions are preferably carried out at below room temperature and in the range of about −20° C. to about 5° C. Compounds of Formula V may be treated with chloroformates or carbonic acid esters to transform the 3+-amino group into a carbamate moiety; or with substituted isocyanates to provide the corresponding urea derivatives. In the foregoing description, when hydrogen halide or a strong acid is expected as a reaction by-product, it is often advantageous to add an amine base to the reaction mixture; suitable amine bases are e.g. pyridine, triethylamine, diisopropyl ethylamine, and dimethylaminopyridine. If it is desired to mask the 4'-hydroxy group of compounds of Formula VI, a variety or phenol protecting groups may be chosen, e.g. benzyl, an acyl group, or acetals. The choice of reagent, the protecting step as well as the removal of the protecting group are discussed in general textbooks such as Theodora Greene's "Protective Groups in Organic Syntheses" (John Wiley and Sons, 1981). It will be appreciated that the phenol protecting methodologies are applicable to compounds of Formula IVb in general.

Aminal compounds of Formula VI wherein $R^5$ is

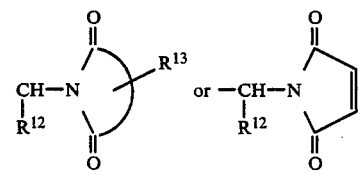

may be prepared by treating the amine of Formula V with a cyclic imide in the presence of at least an equivalent amount of an aldehyde.

According to another aspect of the present invention, there are provided compounds of Formula VI

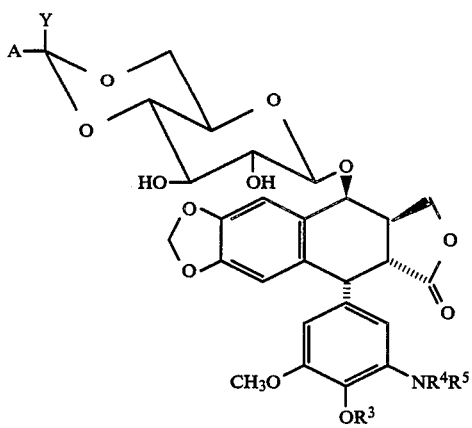

wherein A, Y, and $R^3$ are previously defined, $R^4$ and $R^5$ are independently H or $(C_{1-10})$alkyl with the proviso the $R^4$ and $R^5$ are not both H.

A preferred embodiment provides compounds of Formula VI wherein $R^3$ and $R^4$ are each H.

N-alkylated derivatives of Formula VI may be obtained in several ways. For example, amine V can be directly alkylated e.g. with an alkyl halide to give mono- or di-substituted derivatives. Also as mentioned above, the quinone III can react with an alkylamine to yield the alkyl derivative in addition to amine V. Reduction of amides, imino derivatives, and aminals using chemical reducing agents or catalytic hydrogenation may also be used to prepare monoalkylated derivatives of V which, if desired, may be further alkylated with the same or a different alkyl group; these methods are well-known in the chemical art and may be practiced by a person of ordinary skill in organic synthesis without undue experimentation.

According to another aspect of the present invention, there are provided compounds of Formula VII

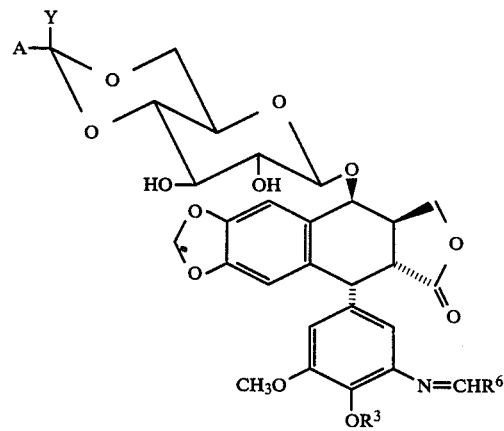

wherein A, Y, $R^3$ and $R^6$ are as previously defined.

a preferred embodiment provides compounds of Formula VII wherein $R^6$ is aryl, substituted aryl, heteroaryl, or substituted heteroaryl.

Imino compounds of Formula VII may be formed when compounds of Formula V are reacted with an aldehyde at room temperature preferably in the presence of an acid catalyst such as p-toluenesulfonic acid, and also preferably employing a method for water removal; suitable methods therefor include the use of a dehydrating agent such as molecular sieves, or the use of azeotropic distillation. Compounds of Formula VII are frequently labile, and a preferred method for their isolation is by chromatography using neutral alumina.

According to another aspect of the present invention, there are provided compounds of Formula VIII and IX which may be obtained when amines of Formula V are reacted with a trialkoxy ortho ester in the presence of an acid catalyst, and with an amide acetal, respectively.

A preferred embodiment provides compounds of Formula VIII wherein $R^{14}$ is H, and compounds of Formula IX where $R^7$ and $R^8$ are both $(C_{1-5})$alkyl.

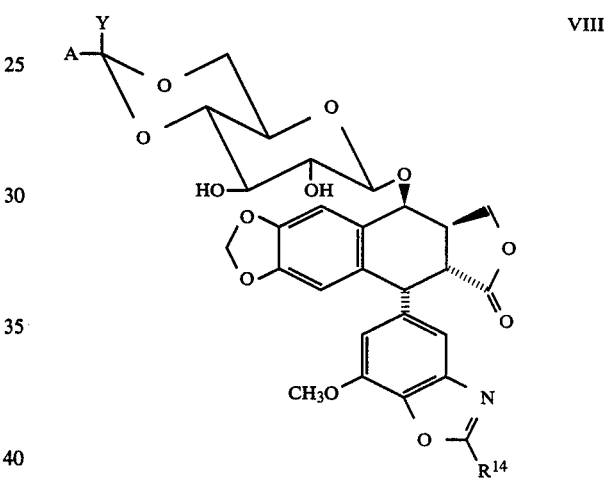

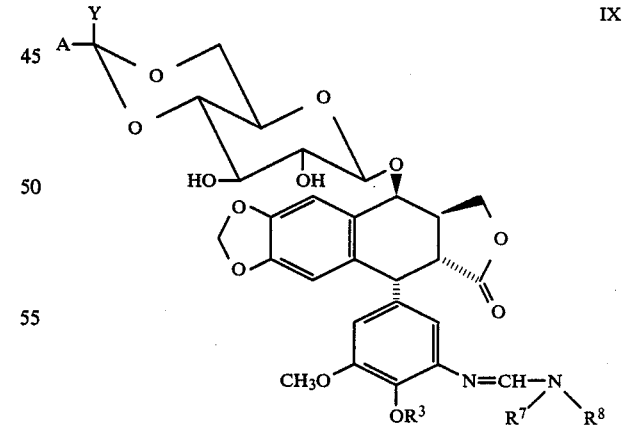

wherein A, Y, $R^3$, $R^7$, $R^8$, and $R^{14}$ are as previously defined.

According to another aspect of the present invention, there are provided compounds of the Formula Xa and Xb

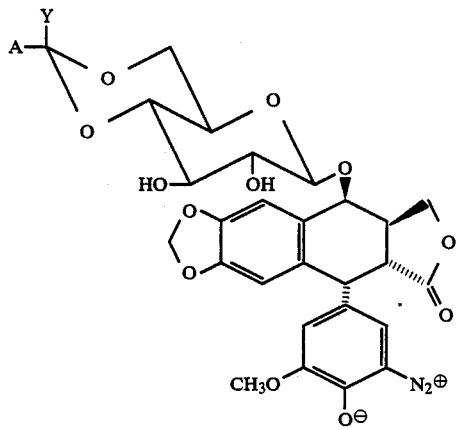

Xa

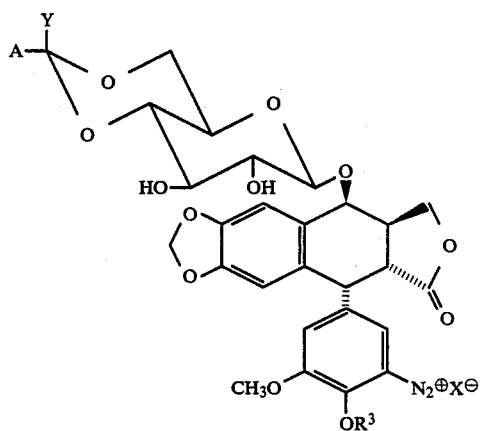

Xb wherein A, Y, X⁻ are as previously defined; $R^3$ is a phenol protecting group.

Compounds of the Formula V may be diazotized in an inert organic solvent at reduced temperature to provide a stable diazonium hydroxide inner salt Xa following aqueous workup. A diazonium salt with a counter ion Xb may be made if the 4'-hydroxyl group is first derivatized e.g. by protection with a conventional phenol protecting group, prior to diazotization.

According to another aspect of the present invention, there are provided 3'-azido and 3'-nitro derivatives having Formula XI and XII, respectively.

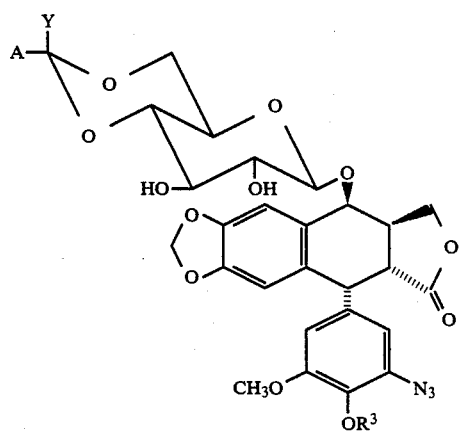

XI

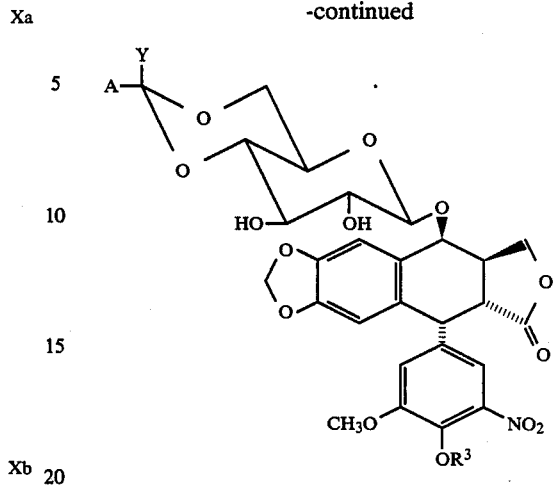

XII wherein A, Y, and $R^3$ are as previously defined.

The azido analog is prepared by displacing the diazonium group with an azide. Oxidation of compounds having the Formula V with a peracid provides the 3'-nitro analogs.

According to another aspect of the present invention, there are provided compounds of Formula XIII which may be prepared from phenol-protected diazonium compound of Formula Xb when treated with an amine; subsequent deprotection yields the 4'-hydroxy-3-triazene compound.

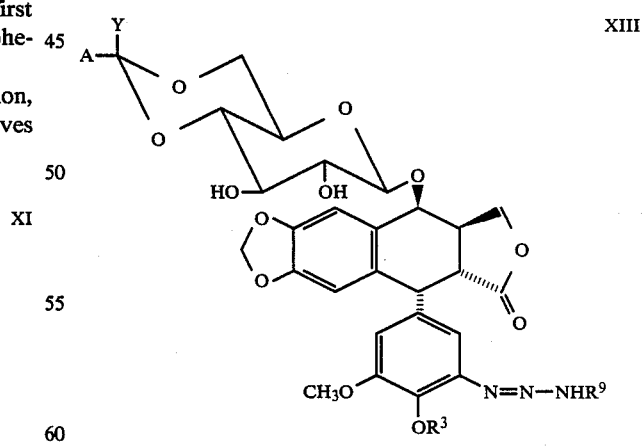

XIII wherein A, Y, $R^3$ and $R^9$ are seen as previously defined.

According to another aspect of the present invention, there are provided compounds of Formula XIV and XV

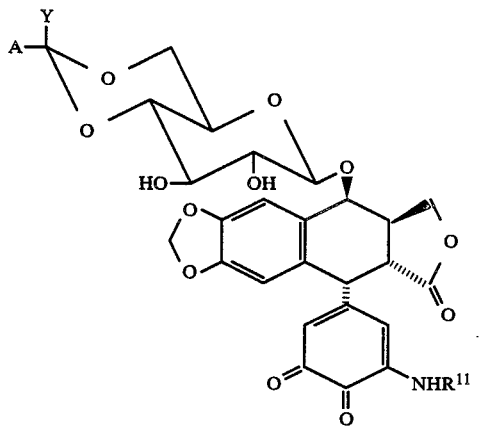

XIV

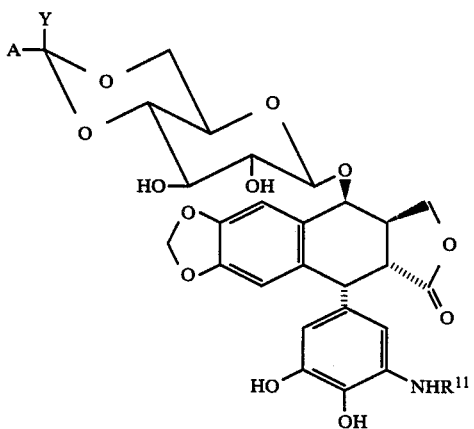

XV wherein $R^{11}$ is an acyl group; A and Y are as previously defined.

A preferred embodiment provides compounds of Formula XIV and XV wherein $R^{11}$ is H, formyl; substituted or unsubstituted alkanoyl; substituted or unsubstituted alkoxycarbonyl; or substituted or unsubstituted (ara)alkylaminocarbonyl.

Compounds of Formula XIV may be prepared by oxidizing compounds of Formula VI wherein $R^3$ and $R^4$ are each H, $R^5$ is acyl. Oxidizing agents such as $NaIO_4/CH_3CN/H_2O$, $NaNO_2/AcOH/THF$, as well as other common oxidants may be used. The compounds of Formula XIV can be readily transformed into the corresponding hydroquinones XV by reduction with a suitable reducing agent such as sodium metabisulfite, or by catalytic hydrogenation.

Another aspect of the present invention provides compounds of the Formula XVI-XIX which may be prepared by the reaction sequence shown in Scheme I. The acyl group of hydroquinones of Formula XV may be removed by conventional methods to provide 3',4'-dihydroxy-5'-amino derivatives of Formula XVI; thus e.g. when $R^5$ is a trichloroethoxycarbonyl group it may be removed with e.g. zinc and acetic acid. Compounds of Formula XVI may then be converted into the 3',4'-dihydroxy-5'-azido derivative of Formula XVIII by the general procedure described supra; refluxing said azido derivative in a chlorinated hydrocarbon solvent provides the corresponding 3'-amino ortho-quinone of Formula XIX; a procedure for converting an azido substituted benzohydroquinone into an amino substituted benzoquinone is described in Moore, H. W. and Shelden, H. R., J. Org. Chem, 1968, 33:4019-24.

Scheme 1

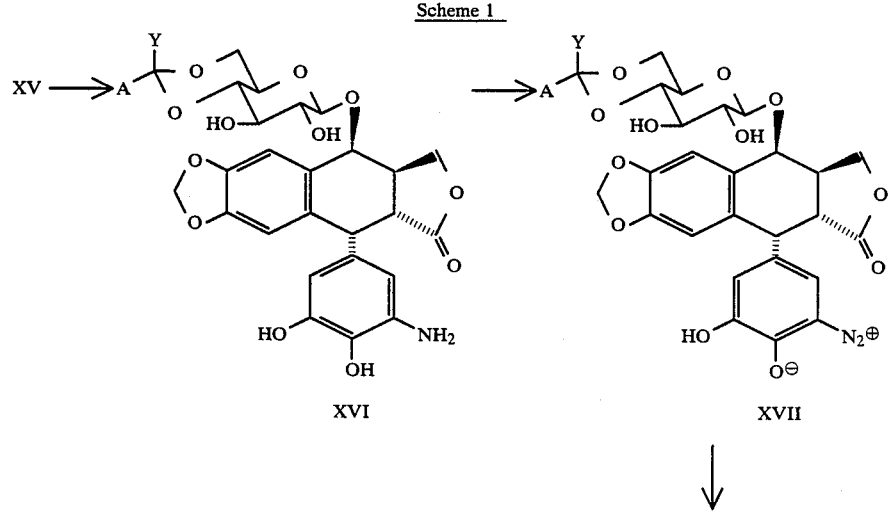

Scheme 1 -continued

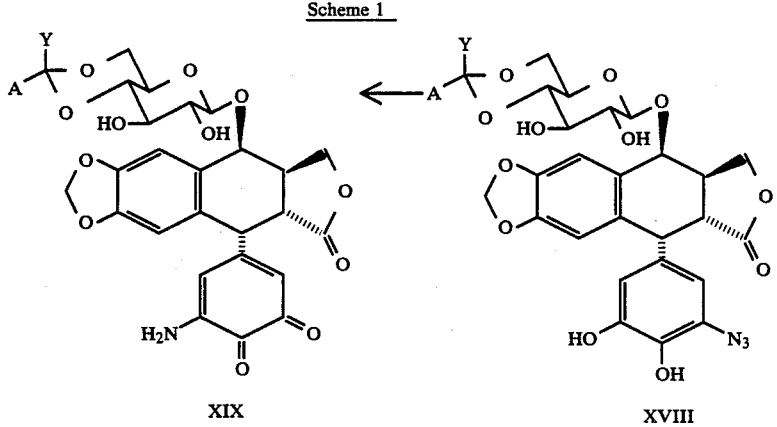

XIX          XVIII

BIOLOGICAL ACTIVITY

Representative compounds of the present invention were evaluated for their antitumor activity in in vitro cytotoxicity assay against human and murine tumor cell lines, as well as against transplantable murine P388 leukemia.

P388 Leukemia.

Female $CDF_1$ mice were implanted intraperitoneally with a tumor inoculum of $10^6$ ascites cells of P388 murine leukemia and treated with various doses of a test compound; four mice were used for each dose level and ten were used as saline-treated control. The compounds were administered by intraperitoneal injection on days 5 and 8 (day 1 being the day of tumor implantation). Antitumor activity was expressed as % T/C which is the ratio of the median survival time (MST) of drug-treated group to the MST of saline-treated control group. A compound showing a % T/C value of 125 or greater is generally considered to have significant antitumor activity in the P388 test. The experiment lasted 31 days at the end of which time the number of survivors was noted. Table I presents the results of the above-described evaluation; only the maximum % T/C and the dose showing the maximum effect are reported.

TABLE I
Antitumor Activity Against Murine P388 Leukemia

| Compound of Example | Dose (mg/kg/inj)* | Max % T/C* |
|---|---|---|
| 1 | 100 | 200 (444) |
| 2 | 50 | 242 |
| 3 | 60 | 228 (444) |
| 4 | 140 (80) | 170 (275) |
| 7 | 70 (80) | 135 (275) |
| 10 | ≧160 (80) | 110 (275) |
| 11 | ≧160 (60) | 110 (280) |
| 12 | 140 (60) | 150 (280) |
| 13 | >200 (80) | 230 (275) |
| 17 | ≧140 (60) | 195 (280) |
| 18 | ≧120 (60) | 200 (280) |
| 19 | ≧200 (60) | 230 (280) |
| 20 | 70-140 (80) | 175 (275) |
| 21 | >200 (60) | 225 (280) |
| 22 | >200 (80) | 235 (275) |
| 24 | 140 (25) | >140 (>140) |
| 25 | >200 (80) | 240 (275) |
| 27 | ≧120 (60) | 165 (280) |
| 28 | 160 (25) | 125 (>140) |

TABLE I-continued
Antitumor Activity Against Murine P388 Leukemia

| Compound of Example | Dose (mg/kg/inj)* | Max % T/C* |
|---|---|---|
| 29 | ≧200 (80) | 135 (275) |

* The values in parentheses are the values obtained with etoposide as the positive control in the same experiment.

Cytotoxicity Assay

The in vitro cytotoxicity assay involved growing various mammalian tumor cells, including human tumor cells, on microtitre plates employing established tissue culture methods. The concentration of each compound required to inhibit cell growth by 50% ($IC_{50}$) was then determined by a four-fold serial dilution technique. The validity of the method has been supported by a report published in the "Proceedings of the American Association for Cancer Research", 1984, 25:1891 (Abst. No. 328). Tumor cells of the following types were employed for each compound tested: B16-F10 murine melanoma; Moser human colon; SW900 human lung and three human colon tumor cell lines namely HCT-116, HCT-VM, and HCT-VP, the latter two being resistant to teniposide (VM) and etoposide (VP), respectively. $IC_{50}$ values less than 500 μg/ml are a positive indicator of antitumor activity. Table II presents $IC_{50}$ values of various compounds of the present invention against the aforementioned cell lines.

TABLE II
In vitro cytotoxicity assay $IC_{50}$ values (μg/ml)*

| | B-16-F10 | HCT-116 | HCT/VM34 | HCT/VP35 | MOSER | SW900 |
|---|---|---|---|---|---|---|
| Example 4 | | | | | | |
| | 13.9 | 16.2 | 23 | 40 | 56 | 63 |
| | 17.9 | 15.7 | 33 | 47 | 49 | 63 |
| Example 7 | | | | | | |
| | 54 | 60 | 63 | 90 | >188 | 78 |
| | 63 | 63 | 65 | 83 | 82 | >188 |
| Example 10 | | | | | | |
| | 57 | 71 | 81 | 92 | 121 | 116 |
| | 87 | 78 | 100 | 106 | >250 | >250 |
| Example 11 | | | | | | |
| | 44 | 58 | 24 | 30 | 89 | 74 |
| | 40 | 98 | 26 | 31 | 93 | 84 |
| Example 12 | | | | | | |
| | 61 | 54 | 59 | 88 | 90 | >188 |
| | 54 | 62 | >188 | 132 | >188 | >188 |
| Example 13 | | | | | | |
| | 5.5 | 3.6 | 2.7 | 3.4 | 12.3 | 11.0 |

TABLE II-continued

In vitro cytotoxicity assay IC$_{50}$ values (μg/ml)*

| B-16-F10 | HCT-116 | HCT/VM34 | HCT/VP35 | MOSER | SW900 |
|---|---|---|---|---|---|
| 8.7 | 4.1 | 3.9 | 3.3 | 12.1 | 8.6 |
| Example 17 | | | | | |
| 6.7 | 12.3 | 23 | 31 | 45 | 22 |
| 8.4 | 10.1 | 24 | 44 | 45 | 44 |
| Example 18 | | | | | |
| 12.5 | 29 | 37 | 55 | 40 | 42 |
| 15.3 | 18.4 | >125 | >125 | 37 | 40 |
| Example 19 | | | | | |
| 16.9 | 13.9 | 21 | 71 | 38 | 42 |
| 16.4 | 12.7 | 19.3 | >188 | 32 | 28 |
| Example 20 | | | | | |
| 13.3 | 9.6 | 92 | 35 | 74 | >188 |
| 19.8 | 5.6 | >188 | 61 | >188 | 78 |
| Example 21 | | | | | |
| 5.3 | 10.0 | 14 | 26 | 25 | 76 |
| 4.3 | 39 | 10.6 | 15.6 | 27 | 33 |
| Example 22 | | | | | |
| 10.9 | 17.0 | 21 | 36 | >250 | >250 |
| 14.1 | 13.3 | 16.2 | 43 | >250 | >250 |
| Example 24[(1)] | | | | | |
| 41 | 43 | 56 | >188 | 92 | 66 |
| 50 | 53 | 82 | 92 | 84 | 90 |
| Example 25 | | | | | |
| 29 | 24 | 38 | 78 | >250 | 76 |
| 25 | 38 | 43 | 102 | 120 | >250 |
| Example 27 | | | | | |
| 5.3 | 10.0 | 14 | 26 | 25 | 76 |
| 4.3 | 39 | 10.6 | 15.6 | 27 | 33 |
| Example 28[(1)] | | | | | |
| 72 | 66 | 58 | 84 | 87 | 80 |
| 81 | 68 | 64 | 70 | 71 | >188 |
| Example 29 | | | | | |
| 39 | 53 | 55 | 77 | 71 | >188 |
| 38 | 46 | 53 | 79 | 77 | >188 |

*The values for etoposide in the same run (other than for compounds of Examples 24 and 28) are 2.7, 1.9 (B16-F10); 2.1, 2.7 (HCT-116); 6.1, 3.1 (HCT/VM34); 30, 41 (HCT/VP35); 38, 39 (Moser); and 67, 12.5 (SW900).
[(1)]The values for etoposide in the same run are 7.0, 4.6 (B16-F10); 9.6, 10.2 (HCT-116); 31, 33 (HCT-VM34); 92, 51 (HCT/VP35); 126, 112 (Moser); and 25, 65 (SW900).

It is apparent from the animal test results provided above that compounds of formula IV possess effective inhibitory action against mammalian tumors. Accordingly, this invention provides a method for inhibiting mammalian tumors which comprises administering an effective tumor-inhibiting dose of an antitumor compound of formula IV to a tumor bearing host.

Another aspect of this invention provides a pharmaceutical composition which comprises an effective tumor-inhibiting amount of an antitumor compound of formula IV and a pharmaceutically acceptable carrier. These compositions may be made up of any pharmaceutical form appropriate for the desired route of administration. Examples of such compositions include solid compositions for oral administration such as tablets, capsules, pills, powders and granules, liquid compositions for oral administration such as solutions, suspensions, syrups or elixirs and preprations for parenteral administration such as sterile solutions, suspensions or emulsions. They may also be manufactured in the form of sterile solid compositions which can be dissolved in sterile water, physiological saline or some other sterile injectable medium immediately before use.

Optimal dosages and regimens for a given mammalian host can be readily ascertained by those skilled in the art. It will, of course, be appreciated that the actual dose used will vary according to the particular composition formulated, the particular compound used, the mode of application and the particular situs, host and disease being treated. Many factors that modify the action of the drug will be taken into account including age, weight, sex, diet, time of administration, route of administration, rate of excretion, condition of the patient, drug combinations, reaction sensitivities and severity of the disease. The following examples are for illustrative purposes only and should not be construed as limiting the scope of the invention.

In the following examples, all temperatures are given in degrees Centigrade. Melting points were recorded on a Thomas-Hoover capillary melting point apparatus and are uncorrected. $^1$H NMR spectra were recorded either on a Bruker WM 360 or a Varian VX2 200 spectrophotometer (using CDCl$_3$ as an internal reference). Chemical shifts are reported in δ units and compling constants in Hertz. Splitting patterns are designated as follows: s, singlet; d, doublet; t, triplet; q, quartet; m, multiplet; bp, broad peak; and dd, doublet of doublet. Infrared spectra were determined either on a Beckman Model 4240 or a Perkin-Elmer 1800 Fourier Transform Infrared Spectrophotometer and are reported in reciprocal centimeters (cm$^{-1}$). Thin-layer chromatography (TLC) was carried out on precoated silica gel plates (60F-254) using UV light and/or iodine vapors as visualizing agents. High and low resolution mass spectra were recorded on KRATOS MS 50 and KRATOS MS 25RFA Spectophotometer, respectively. "Flash Chromatography" refers to the method described by Still (Still, W. C. et al, J. Org. Chem., 1978, 43:2923) and was carried out using either E. Merck silica gel (200-400 mesh) or Woelm silica gel (32-63 μm). All evaporations of solvents were performed under reduced pressure.

EXAMPLE 1

Etoposide-ortho-quinone-3'-O-methyloxime (IVa; A=R$^1$=methyl; Y=H)

A solution of etoposide ortho-quinone IIIa (350 mg, 0.611 mmol) in pyridine (20 ml) was treated with a solution of methoxylamine hydrochloride (350 mg, 4.19 mmol) in pyridine (10 ml). The resultant orange solution was stirred for 30 minutes at room temperature and the pyridine was then removed in vacuo. The residue was dissolved in CH$_2$Cl$_2$ (50 ml) and partitioned with H$_2$O (20 ml) and 1N HCl (10 ml). The aqueous layer was further extracted with CH$_2$Cl$_2$ (25 ml) and the combined organic extracts were dried over MgSO$_4$. The solvent was evaporated in vacuo to give a dark orange oil. Flash chromatography on silica gel (14 g) with 5% CH$_3$OH in CH$_2$Cl$_2$ gave 243 mg (66%) of the title compound as an orange solid. Trituration with Et$_2$O provided the analytical sample. On a larger scale, this oxime is generally not purified but is directly hydrogenated to the amine Va in an overall yield of ca 70%.

IR (KBr) 3480, 1775, 1670, 1625, 1488, 1237, 1040 cm$^{-1}$.

$^1$H NMR (CDCl$_3$) δ 6.82 (s,1H), 6.56 (s,1H), 6.48 (d,1H), 6.07 (d,1H), 6.01 (d,1H) 5.75 (d,1H), 4.92 (d,1H), 4.76 (q,1H), 4.66 (d,1H), 4.50 (dd,1H), 4.38 (dd,1H), 4.27 (d,1H), 4.22-4.17 (m,1H), 4.15 (s,3H), 3.79 (s,3H), 3.78-3.74 (m,1H), 3.63-3.58 (m,1H), 3.44 (dd,1H), 3.38-3.30 (m,3H), 2.95-2.87 (m,1H), 1.40 (d,3H).

Anal. Calcd for C$_{29}$H$_{31}$NO$_{13}$: C,57.90; H,5.19; N,2.33. Found: C,56.01; H,5.04; N,2.41.

EXAMPLE 2

Etoposide-ortho-quinone-3'-O-benzyloxime (IVa; A=methyl; Y=H; $R^1$=benzyl)

The general procedure of Example 1 was followed, except O-benzylhydroxylamine hydrochloride was used in place of methyloxylamine hydrochloride, to afford the title comopound.

EXAMPLE 3

3'-Amino-3'-desmethoxy etoposide (Va)

The crude oxime obtained from etoposide ortho-quinone IIIa (4.1 g. 7.3 mmol) and methoxyamine hydrochloride (4.1 g, 49 mmol) by the procedure described in Example 1 was dissolved in reagent alcohol (275 ml) and treated with 20% palladium hydroxide on carbon (290 mg) and 10% palladium on carbon (1.6 g). The mixture was hydrogenated at 40–50 psi $H_2$. After 16 h, the mixture was filtered through Celite, washed with ethyl acetate, and the solvent was evaporated. The crude product ws purified by flash chromatography on 300 g. E. Merck 230–400 mesh silica gel using 8:2 EtOAc/hexane as eluent to provide 2.89 g (70% overall) of the title compound as a white solid. Recrystallization from ethanol gave the analytical sample.

IR (KBr) 3455, 1775, 1615, 1490, 1235, 1070, 1030, 1000, 930 cm$^{-1}$. $^1$H NMR (CDCl$_3$) δ 6.76 (s,1H), 6.48 (s,1H), 6.37 (d,1H), 5.96 (ABq,2H), 5.65 (d,1H), 4.87 (d,1H), 4.73 (q,1H), 4.61 (d,1H), 4.47 (d,1H), 4.38 (dd,1H), 4.23–4.16 (m,2H), 3.78 (s,3H), 3.76–3.72 (m,1H), 3.60–3.55 (m,1H), 3.42 (dd,1H), 3.37–3.30 (m,2H), 3.21 (dd,1H), 2.97–2.88 (m,1H), 1.37 (d,3H).

Anal. Calcd for $C_{28}H_{31}NO_{12}$: C,58.63; H,5.45; N,2.44. Found: C57.85; H,5.76; N,2.35

EXAMPLE 4

3'-Desmethoxy-3'-methylamine etoposide (VI; A=$R^5$=methyl; Y=$R^3$=$R^4$=H)

A solution of 40% aqueous methylamine (1 ml, 12.80 mmol) in MeOH (4 ml) was added over 3 minutes to a solution of etoposide ortho-quinone IIIa (0.25 g, 0.437 mmol) in MeOH (50 ml) stirring at room temperature. The dark red solution became dark brown. After 30 minutes the solution was concentrated, and purified by preparative chromatography on silica gel using 5% MeOH in CH$_2$Cl$_2$ as eluent. Isolation of the two most intense UV active bands provided the two major products of the complex mixture. The top isolated band provided the title compound (45 mg, 18%) as an off-white solid.

$^1$H NMR (CDCl$_3$) δ 6.82 (s,1H), 6.38 (s,1H), 6.16 (s,1H), 5.94 (m,2H), 5.85 (s,1H), 4.95 (d,J=3.2Hz,1H), 4.75 (m1H), 4.70–4.32 (m,3H), 4.21 (m,2H), 4.78 (s,3H), 4.75–2.85 (m,7H), 2.72 (s,3H), 1.40 (d,J=5.0Hz,1H).

The lower isolated band (51 mg, 20%) provided the compound of Example 3.

EXAMPLE 5

3'-Butylamino-3'-desmethoxy etoposide (VI; A=methyl; Y=$R^3$=$R^4$=H, $R^5$ is butyl)

The general procedure of Example 4 was followed, except n-butylamine was used, to provide the title compound and the compound of Example 3.

MS (EI) m/e$^+$ =630 (m+1)$^+$.

Partial $^1$H spectrum (CDCl$_3$): δ 6.80 (s,1H), 6.54 (s,1H), 6.14 (bs,1H), 5.94 (d,2H), 5.78 (bs,1H), 3.75 (s,3H), 1.36 (d,3H), 0.89 (t,3h).

EXAMPLE 6

3'-Desmethoxy-3'-formylamino etoposide (VI; A=methyl; $R^3$=$R^4$=Y=H; $R^5$=formyl)

A solution of acetic formic anyhdride was prepared by adding formic acid (98%, 0.60 ml, 16 mmol) to acetic anhydride (1.23 ml, 13 mmol) stirring at room temperature under $N_2$. The solution was kept at 55° C. for 1.5 hour and then allowed to cool to room temperature. A portion of this reagent (0.45 ml) was then added dropwise to a solution of 3'-aminoetoposide Va (0.26 g, 0.454 mmol) in dry THF (4 ml) stirring at 2° C. under $N_2$. The reaction mixture was stirred for 2 hours and allowed to warm to 10° C. over a period of 1 hour. The reaction mixture was poured into $H_2O$ (50 ml) and extracted with one 60 ml portion of $CH_2Cl_2$ and then one 30 ml portion of EtOAc. The combined organic extracts were dried in vacuo. Flash chromatography on silica gel using 3% then 4% MeOH in $CH_2Cl_2$ as eluent and isolation of the material having a TLC rf slightly lower than the starting amine in 10% MeOH in $CH_2Cl_2$ provided 0.213 g (78%) of a faintly pink solid: mp. 216°–220°.

IR (KBr) 3430 (b), 2940, 1780, 1690 cm$^{-1}$.

$^1$H NMR (CDCl$_3$) δ 8.46 (bs,1H), 8.45, 8.19 (pair of singlets, 1H,formyl H), 7.80 (bm,1H), 6.95, 6.85, 6.71, 6.58, 6.53, 6.15, (singlets, total integ. 4H), 5.98 (bs,2H), 5.05 (m,1H), 4.78 (d,J=4.9Hz,1H) 4.69–4.40 (m,3H), 4.38–4.10 (m,2H), 3.86, 3.83 (s,1H), 3.80–3.51 (m,2H), 3.60–3.30 (m,4H), 3.02 (bm,1H), 1.39 (d,J=4.9H,3H).

FAB MS m/e (relative intensity) 602 (MH$^+$).

EXAMPLE 7

3'-Acetylamino-3'-desmethoxy etoposide (VI; A=methyl; Y=$R^3$=$R^4$=H; $R^5$=acetyl)

Acetic anhydride (0.065 ml, 0.69 mmol) was added dropwise to a solution of 3'-aminoetoposide Va (0.420 g, 0.70 mmol) in 14 ml of dry $CH_2Cl_2$ stirring at 2° C. under $N_2$. The reaction mixture was stirred for 5.5 hours at 2° C. and then an additional 0.01 ml (0.11 mmol) of acetic anhydride was added. The reaction mixture was stirred for 1 hour at 2° C. and then poured into a solution containing 25 ml of $H_2O$ and 25 ml of saturated aqueous NaHCO$_3$. The mixture was extracted with three 50 ml portions of $CH_2Cl_2$ and the combined organic layers were washed with saturated aqueous NaCl and dried over anhydrous MgSO$_4$. Concentration and flash chromatography on silica gel using 3% then 4% MeOH in $CH_2Cl_2$ as eluent provided 19.3 mg of an unidentified side product (TLC rf=0.17; 5% MeOH in CH$_2$Cl$_2$) and 0.328 g (73%) of the title compound as an off-white powder: TLC rf=0.14; 5% MeOH in CH$_2$Cl$_2$; mp. 225°–227°.

IR (KBr) 3350–3080, 2960, 1770 cm$^{-1}$.

$^1$H NMR (CDCl$_3$) δ 8.45 (s,1H), 8.23 (bs,1H), 6.76 (s,1H), 6.61 (s,1) 6.49 (s,1H), 6.38 (s,1H), 5.84 (d,J=8.6Hz, 2H), 4.86 (d,J=3.2Hz,1H), 4.63 (m,1H), 4.30–4.15 (m,3H), 4.15–4.05 (m,2H), 3.72 (s,3H), 3.6–3.4 (m,2H), 3.4–3.25 (m,4H), 2.86 (m,1H), 2.19 (s,3H), 1.26 (d,J=5.0Hz,3H).

EXAMPLE 8

3'-Desmethoxy-3'-trifluoroacetylamino etoposide (VI; A=methyl; Y=R$^3$=R$^4$=H; R$^5$=trifluoroacetyl)

Trifluoracetic anhydride (76 mg, 0.362 mmol) was added dropwise over 1 minute to a solution of 3'-aminoetoposide Va (200 mg, 0.349 mmol) in dry CH$_2$Cl$_2$ (10 ml) and pyridine (50 μl) stirring at 0° C. under N$_2$. The mixture was stirred at 0° C. for 30 minutes and then at room temperature for 2 hours. The mixture was partitioned with pH 7 phosphate buffer (75 ml) and CH$_2$Cl$_2$ (75 ml). The organic portion was washed with brine (75 ml), dried over Na$_2$SO$_4$, and the solvent evaporated in vacuo. Preparative TLC on silica gel (5% CH$_3$OH in CH$_2$Cl$_2$) gave 149.7 mg (64.1%) of the pure title compound as a white solid, mp. 209°–212° C.

IR (KBr) 3420, 1775, 1735, 1625, 1510, 1490, 1237, 1165, 1082, 1045, 1010, 940, 878, 702 cm$^{-1}$.

$^1$H NMR (CDCl$_3$) δ 7.03 (d,1H), 6.99 (d,1H), 6.82 (s,1H), 6.49 (s,1H), 6.00 (br s,2H), 4.97 (d,1H), 4.74 (q,1H), 4.66 (d,1H), 4.57 (d,1H), 4.42 (dd,1H), 4.30–4.14 (m,2H), 3.92 (s,3H), 3.75 (m,1H), 3.56 (m,1H), 3.49–3.17 (m,4H), 3.09–2.92 (m,1H), 1.38 (d,3H).

Anal. Calcd for C$_{30}$H$_{30}$F$_3$NO$_{13}$: C, 53.82; H, 4.52; N, 2.09. Found: C, 53.62 ; H, 4.44; N, 1.96.

EXAMPLE 9

3'Desmethoxy-3'-[[(2,2,2-trichloroethyl)oxy]carbonyl]amino etoposide (IVb; A=methyl; Y=R$^3$=R$^4$=H; R$^5$=2,2,2-trichloroethoxycarbonyl)

Trichloroethyl chloroformate (0.10 ml, 0.73 mmol) was added dropwise via syringe to a solution of 3'-aminoetoposide Va (0.40 g, 0.70 mmol) and pyridine (90 μl, 1.11 mmol) in 5 ml of CH$_2$Cl$_2$ stirring at 2° C. under N$_2$. The reaction mixture was stirred for 5 hours at temperatures between 2° and 10° C. and then an additional 10 μl of trichloroethyl chloroformate was added and the reaction mixture was stirred for 15 hours at room temperature. The reaction mixture was poured into 50 ml of water and extracted with 3 portions of 50 ml each of CH$_2$Cl$_2$. The combined organic layers were dried over anhydrous MgSO$_4$ and then purified by flash chromatography on silical gel using 3% MeOH in CH$_2$Cl$_2$ as eluent. Isolation of the major, less polar product provided 0.32 g (62%) of a yellow solid, mp. decomp above 220° C.

IR (KBr) 3440, 2910, 1780 (b), 1625, 1552 cm$^{-1}$.

$^1$H NMR (CDCl$_3$) δ 7.12 (m,1H), 6.83 (m,2H), 6.49 (s,1H), 5.95 (m,2H), 5.65 (s,1H), 4.94 (d,J=3.28Hz,1H), 4.80–4.60 (m,4H), 4.54 (d,J=5.3Hz,1H), 4.38 (m,1H), 4.23–4.05 (m,2H), 3.94 (s,3H), 3.72 (m,1H), 3.52 (m,1H), 3.43 (m,1H), 3.32 (m,2H), 3.23 (dd,J=14.2, 5.4Hz,1H), 3.01 (m,1H), 2.68 (s,1H), 2.41 (s,1H), 1.38 (d,J=2.4Hz,3H).

MS (FAB) m/e 748 (M+H)$^+$

EXAMPLE 10

3'-[(2-Chloroethylamino)carbonyl]amino-3'-desmethoxy etoposide (VI; A=methyl; Y=R$^3$=R$^4$=H, R$^5$=2-chlorethylaminocarbonyl)

To a solution of 3'-aminoetoposide Va (0.40 g, 0.69 mmol) stirring at 20° C. under N$_2$ in 4 ml of dry CH$_2$Cl$_2$ was added 2-chloroethyl isocyanate (62 1, 0.76 mmol) dropwise via syringe. A white precipitate began to form immediately upon addition. The reaction mixture was stirred for 4 hours at 20° C. and then 15 minutes at 0° C. Suction filtration and drying in vacuo provided 0.32 g (68%) of an off-white amorphous solid: mp. 195°–197° C.

IR (KBr) 3400 (b), 2920, 1770, 1660 cm$^{-1}$.

$^1$H NMR (CDCl$_3$/DMSO) δ 8.97 (bs,1H) 7.87 (s,1H), 6.71 (s,1H), 6.54 (t,J=5.6Hz,1H), 6.33 (s,1H), 6.31 (s,1H), 6.24 (s,1), 5.78 (ABQ,J$_{AB}$=5.5Hz,2H), 4.79 (d,J=5.3Hz,1H), 4.58 (m,1H), 4.51–4.24 (m4H), 4.06–3.98 (m,2H), 3.61 (s,3H), 3.45–3.33 (m,6H), 3.24–3.12 (m,4H), 2.80–2.76 (m,1H), 1.21 (d,J=2.7Hz,1H).

MH$^+$ calcd. for C$_{31}$H$_{35}$O$_{13}$N$_2$Cl: 678.1828; Found: 678.1826.

EXAMPLE 11

3'-Desmethoxy-3'-([[phenylmethyl]amino]carbonyl]amino etoposide (VI; A=methyl; Y=R$^3$=R$^4$=H; R$^5$=benzylaminocarbonyl)

Triethylamine (0.25 ml), followed by benzyl isocyanate (50 μl, 0.40 mmol), was slowly added to a solution of 3'-aminoetoposide Va (200 mg, 0.349 mmol) in 9:1 CH$_2$Cl$_2$/THF. After 20 minutes the resultant precipitate was collected by filtration, washed with cold EtOAc and dried to afford 150 mg (61%) of the title compound as a colorless solid.

$^1$H NMR (CDCl$_3$) δ 7.33–7.18 (m,6H), 7.01 (s,1H), 6.55 (d,1H), 6.51 (s,1H), 6.00 (d,2H), 5.22 (d,2H), 4.92 (d,1H), 4.71 (q,1H), 4.59 (d,1H,J=7.7Hz), 4.49 (d,1H,J=5.5Hz), 4.31–4.07 (m,3H), 3.67 (s,3H), 3.49–2.95 (m,7H), 1.37 (d,3H).

EXAMPLE 12

3'-Desmethoxy-3'-methanesulfonamido etoposide (VI; A=methyl; Y=R$^3$=R$^4$=H; R$^5$=methanesulfonyl)

Methanesulfonyl chloride (31 1, 0.384 mmol) was added dropwise to a solution of 3'-aminoetoposide Va (0.22 g, 0.384 mmol) and pyridine (0.10 ml, 1.24 mmol) in 9 ml of dry CH$_2$Cl$_2$ stirring at −20° C. under N$_2$. The reaction was stirred for 3 hours at −20° C. and allowed to warm to 20° C. over 1 hour with stirring. The reaction mixture was poured into 50 ml of water and extracted with one 50 ml portion and then two 10 ml portions of CH$_2$Cl$_2$. The combined organic extracts were dried over anhydrous MgSO$_4$ concentrated in vacuo. Flash chromatography using 3% then 4% MeOH in CH$_2$Cl$_2$ as eluent provided 0.139 g (56%) of an off-white solid: mp. 208°–211° C. (white solid to pink foam).

IR (KBr) 3460 (b), 2925, 1779, 1620, 1340, 1163 cm$^{-1}$.

$^1$H NMR (CDCl$_3$/DMSO) δ 7.04 (s,1H), 6.97 (s,1H), 6.77 (s,1H), 6.66 (d,J=1.7Hz,1H), 6.41 (s,1H), 6.37 (d,J=1.7Hz,1H), 5.89 (m,2H), 4.89 (d,J=3.4Hz,1H), 4.67 (m,1H), 4.66 (m,2H), 4.40 (m,1H), 4.17 (m,2H), 3.82 (s,3H), 3.66 (t,J=8.8Hz,1H), 3.39–3.28 (m,4H), 2.90 (m,1H), 2.85 (s,3H), 1.32 (d,J=5.0Hz,3H).

FAB MS m/e (relative intensity) 652 (MH$^+$).

EXAMPLE 13

3'-Desmethoxy-3'-[(N-succinimido)methyl]amino etoposide (VI; A=methyl; Y=R$^3$=R$^4$=H; R$^5$=(N-succinimido)methyl)

A solution of 3'-aminoetoposide Va (0.30 g, 0.52 mmol) and succinimide (0.052 g, 0.52 mmol) in 4 ml of anhydrous absolute ethanol under N$_2$ was brought to reflux and 0.040 ml (0.52 mmol) of 37% aqueous formaldehyde was added. The reaction mixture was refluxed for 4 hours during which time a white precipitate formed. The reaction mixture was cooled to 0° C., filtered by suction, and the residue washed with 5 ml of cold EtOH to provide 0.272 g, (76%) of an off-white solid: mp. 210°–212° C.

IR (KBr) 3435 (b), 2920, 1780, 1705, 1620 cm$^{-1}$.

$^1$H NMR (CDCl$_3$/DMSO) δ 6.81 (s,1H), 6.40 (s,2H), 5.80 (d,J=7.9Hz,2H), 5.83 (s,1H), b 5.82 (s,1H), 5.04–4.97 (m,2H (1 exchangeable)), 4.73–4.67 (m,3H), 4.51 (d,J=7.6Hz,1H), 4.38 (m,2H), 4.14 (t,J=8.3Hz,2H), 3.97 (d,J=2.9 Hz,1H), 3.75 (s,3H), 3.61 (t,J=2.2Hz,1H), 3.53 (t,J=9.0 Hz,1H), 3.36–3.25 (m,4H), 2.99 (bm,1H), 2.51 (m,4H), 1.32 (d,J=5.0Hz,3H).

MH$^+$ cacld. for C$_{33}$H$_{36}$O$_{14}$N$_2$: 684.2167; Found: 684.2151.

EXAMPLE 14

3'-Desmethoxy-3'-[N-(3-octylthio)succinimido]methylamino etoposide (VI; A=methyl, Y=R$^3$=R$^4$=R$^5$=H; R$^5$=[N-(3-octylthio)succinimido]methyl)

Formalin (26 μl, 0.35 mmol) was added to a solution of 3'-aminoetoposide Va (0.20 g 0.35 mmol) and 3-octylthio succinimide (0.085 g, 0.35 mmol) stirring at reflux in 6 ml of EtOH. The reaction mixture was refluxed for 3 hours and then allowed 5 mg of the succinimide and 5 μl of formalin were added and the reaction mixture was refluxed for 1 hour, and then cooled to room temperature. Removal of ethanol in vacuo followed by flash chromatography using 4% MeOH in CH$_2$Cl$_2$ on silica gel provided the product as a white powder (0.111 g, 38%), mp. HPLC analysis showed the presence of two diastereomers (1:1).

IR (KBr) 3480, 2962, 2925, 1781, 1707, 1621, 1520, 1490 cm$^{-1}$.

$^1$H NMR (CDCl$_3$) δ 6.83, 6.81 (s,1H), 6.49, 6.47 (s,1H), 6.45 (s,1H), 5.95 (m,2H), 5.84, 5.81 (s,1H), 5.33 (s,1H), 5.01 (m,2H), 4.80–4.70 (m,2H), 4.62 (m,1H), 4.45 (m,1H), 4.37 (m,1H), 4.15 (m,2H), 3.80 (s,3H), 3.68 (m,1H), 3.57 (m,2H), 3.41 (m,1H), 3.19 (m,2H), 3.04 (m,1H), 3.02 (m,2H), 2.82 (m,1H), 2.62–2.30 (m,4H), 1.60–1.40 (m,2H), 1.37 (d,J=2.4Hz,3H), 0.86 (t,J=6.3Hz,3H).

EXAMPLE 15

3'-Desmethoxy-3'-[(N-maleimido)methyl]amino etoposide (VI; A=methyl; Y=R$^3$=R$^4$=H; R$^5$=maleimidomethyl)

A similar procedure as in Example 14 was followed except the 3-octylthiosuccinimide was replaced by maleimide to give, after chromatography, a 68% yield of a faintly yellow powder.

IR (KBr) 3440, 2918, 1775, 1710, 1616, 1505, 1486 cm$^{-1}$.

$^1$H NMR (CDCl$_3$) δ 6.85 (s,1H), 6.57 (s,1H), 6.56 (s,2H), 6.45 (s,1H), 5.95 (m,2H), 5.76 (s,1H), 5.31 (s,1H), 5.01 (d,J=3.3Hz,1H), 4.91 (m,1H), 4.78–4.66 (m,3H), 4.47 (d,J=5.3Hz,1H), 4.37 (m,1H), 4.18 (m,2H), 3.82 (s,3H), 3.74 (m,1H), 3.55 (m,1H), 3.43 (m,1H), 3.22 (m,2H), 3.20 (dd,J=7.0, 5.26Hz,1H), 3.05 (m,1H), 2.68 (s,1H), 2.41 (s,1H), 1.38 (d,J=4.9Hz,3H).

MS (FAB) m/e 682 M$^+$.

EXAMPLE 16

3'-Desmethoxy-3'-[N-[3-(2-pyridyl)thio]succinimido]methylamino etoposide (VI; A=methyl; Y=R$^3$=R$^4$=H; R$^5$=[N-[3(2-pyridyl)thio]succinimido]methyl)

A similar procedure as in Example 14 was followed except the 3-octylthiosuccinimide was replaced by 3-(2-pyridyl)thiosuccinimide to give a cream colored solid: mp. slow decomposition above 185° C.

EXAMPLE 17

3'-Desmethyoxy-3'-[(3-thienyl)methylene]amino etoposide (VII; A=methyl; Y=R$^3$H; R$^6$=3-thienyl)

A mixture of 3'-aminoetoposide Va (222 mg, 0.387 mmol), anhydrous MgSO$_4$ (2.0 g), activated 4A molecular sieves (2.7 g) and p-toluenesulfonic acid monohydrate (11 mg) was treated under N$_2$ with dry CH$_2$Cl$_2$ (30 ml), and 3-thiophenecarboxaldehyde (3.37 g, 30.1 mmol) was then added neat via syringe. The mixture was stirred in the dark for 7 days at room temperature, filtered, and the solids were washed with CH$_2$Cl$_2$ (10 ml) and EtOAc (25 ml). The filtrate was concentrated to a volume of ca 15 ml and applied to the top of a 3 cm column filled with 4½" of Woelm neutral alumina. Elution with CH$_2$Cl$_2$ (250 ml) followed by 5% CH$_3$OH in CH$_2$Cl$_2$ gave 95.0 mg (37%) of the title compound as a yellow-brown solid, mp 190°–195° C. (dec).

IR (KBr) 3445, 1775, 1630, 1605, 1510, 1495, 1290, 1240, 1165, 1085, 1045, 1008, 940, 875, 805, 700 cm$^{-1}$.

$^1$H NMR (CDCl$_3$) δ 8.45 (s,1H), 7.77 (d,1H, J=2.9Hz), 7.64 (d,1H,J=5.2Hz), 7.35 (dd,1H,J=2.9 and 5.2Hz), 6.81 (s,1H), 6.58 (d,1H,J=1.6Hz), 6.54 (s,1H), 6.40 (d,1H,J=1.6Hz), 5.97 (d,2H), 4.91 (d,1H,J=3.5Hz), 4.75 (q,1H,J=5.0Hz), 4.65 (d,1H,J=7.5Hz), 4.61 (d,1H,J=5.3Hz), 4.41 (dd,1H), 4.22 (dd,1H), 4.16 (dd,1H), 3.81 (s,3H), 3.74 (dd,1H), 3.56 (dd,1H), 3.43 (dd,1H), 3.34–3.31 (m,2H), 3.26 (dd,1H,J=5.3 and 14.0Hz), 2.94–2.88 (m,1H), 1.38 (d,3H,J=5.0Hz).

EXAMPLE 18

3'-Desmethoxy-3'-[(2-furyl)methylene]amino etoposide (VII; A=methyl; Y=R$^3$=H; R$^6$=2-furyl)

The procedure described in Example 19 was followed using 3'-aminoetoposide Va (213 mg, 0.371 mmol), anhydrous MgSO$_4$ (2.0 g), activated 4A molecular sieves (2.5 g), p-toluenesulfonic acid monohydrate (13 mg), 2-furancarboxaldehyde (3.39 g, 35.2 mmol), and CH$_2$Cl$_2$ (30 ml). After 72 hours at room temperature the mixture was worked up and purified as described in Example 19 to give 79.0 mg (33%) of the title compound as a yellow-orange solid.

IR (KBr) 3440, 1775, 1630, 1603, 1508, 1488, 1285, 1235, 1162, 1080, 1023, 935, 893, 765, 705 cm$^{-1}$.

$^1$H NMR (CDCl$_3$) δ 8.30 (s,1H), 7.57 (d,1H,J=1.5Hz), 6.95 (d,1H,J=3.5Hz), 6.80 (s,1H), 6.66 (d,1H,J=1.5Hz), 6.53 (s,1H), 6.34 (d,1H,J=1.5Hz), 5.97 (d,2H), 4.89 (d,1H,J=3.4Hz), 4.73 (q,1H,J=5.0Hz), 4.65 (d,1H,J=7.5Hz), 4.60 (d,1H,J=5.3Hz), 4.41 (dd,1H), 4.23–4.13 (m,2H), 3.83 (s,3H), 3.75 (dd,1H), 3.56 (dd,1H), 3.43 (dd,1H), 3.34–3.31 (m,2H), 3.25 (dd,1H,J=5.3 and 14.1Hz), 2.93–2.88 (m,1H), 1.38 (d,3H,J=5.0Hz).

EXAMPLE 19

3'-Desmethoxy-3'-[(4-pyridyl)methylene]amino etoposide (VII; A=methyl; Y=R$^3$=H; R$^6$=4-pyridyl)

A mixture of 3'-aminoetoposide Va (215 mg, 0.375 mmol), activated 4A molecular sieves (2.1 g) and 4-pyridinecar-boxaldehyde (3.8 g, 35.5 mmol) in dry CH$_2$Cl$_2$ (38 ml) was stirred at room temperature for 7 days and then applied directly to the top of a 2 cm column filled with 6½" of Woelm neutral alumina. Elution with CH$_2$Cl$_2$ (250 ml) followed by 1:1 EtOAc in CH$_2$Cl2 (250 ml) removed the excess aldehyde; further elution with 5–6% CH$_3$OH in CH$_2$Cl$_2$ gave 114.2 mg (46%) of the title compound as a yellow-orange solid, mp 198°–204° C. (dec).

IR (KBr) 3440, 1775, 1608, 1490, 1388, 1292, 1238, 1165, 1085, 1040, 1010, 940, 705 cm$^{-1}$.

$^1$H NMR (CDCl$_3$) δ 8.72 (d,2H,J=4.5Hz), 8.49 (s,1H), 7.70 (d,2H,J=4.5Hz), 6.82 (s,1H), 6.65 (s,1H), 6.63 (d,1H,J=1.7Hz), 6.54 (s,1H), 6.49 (d,1H,J=1.7Hz), 5.98 (d,2H), 4.92 (d,1H,J=3.5Hz), 4.73 (q,1H,J=5.0Hz), 4.66 (d,1H,J=7.6Hz), 4.62 (d,1H,J=5.3Hz), 4.42 (dd,1H), 4.25–4.15 (m,2H), 3.82 (s,3H), 3.77 (m,1H), 3.56 (dd,1H), 3.44 (dd,1H), 3.34–3.20 (m,3H), 2.91–2.87 (m,1H), 1.38 (d,3H,J=5.0Hz).

EXAMPLE 20

3'-Desmethoxy-3'-[[(4-methoxy)phenyl]methylene]amino etoposide (VII; A=methyl; Y=R$^3$=H; R$^6$=p-methoxyphenyl)

A solution of 3'-aminoetoposide Va (260 mg, 0.453 mmol), p-anisaldehyde (4.1 g, 30.1 mmol), and p-toluenesulfonic acid monohydrate (7.0 mg) in dry CH$_2$Cl$_2$ (70 ml) was refluxed for 6 hours in a flask equipped with a Soxhlet extractor filled with 4.8 g of activated 4A molecular sieves. The mixture was then treated with 0.31 g of activated 4A molecular sieves and stirred at room temperature for 13 days. The reaction mixture was applied directly to the top of a 2 cm column filled with 20.5 g of Woelm neutral alumina. Elution with CH$_2$Cl$_2$ (400–500 ml) followed by 2% CH$_3$OH in CH$_2$Cl$_2$ gave 175 mg (56%) of the title compound as an analytically pure pale yellow solid, mp 173°–178° C. (dec).

IR (KBr) 3450, 1775, 1605, 1390, 1260, 1235, 1168, 1080, 1040, 940, 840, 705 cm$^{-1}$.

$^1$H NMR (CDCl$_3$) δ 8.37 (s,1H), 7.81 (d,2H), 6.94 (d,2H), 6.81 (s,1H), 6.57 (d,1H), 6.55 (s,1H), 6.41 (d,1H), 5.97 (d,2H), 4.91 (d,1H), 4.73 (q,1H), 4.65 (d,1H), 4.61 (d,1H), 4.41 (dd,1H), 4.23–4.13 (m,2H), 3.85 (s,3H), 3.81 (s,3H), 3.74 (dd,1H), 3.56 (dd,1H), 3.43 (dd,1H), 3.34–3.31 (m,2H), 3.25 (dd,1H), 2.94–2.87 (m,1H), 1.37 (d,3H).

Anal. Calcd for C$_{36}$H$_{37}$NO$_{13}$: C,62.51; H,5.39; N,2.02. Found: C,62.48; H,5.67; N,2.11.

EXAMPLE 21

3'-Desmethoxy-3'-[[(3,4,5-trimethoxy)phenyl]methylene]amino etoposide (VII; A=methyl; Y=R$^3$=H; R$^6$=3,4,5-trimethoxyphenyl)

A mixture of 3'-aminoetoposide Va (145 mg, 0.253 mmol), 3,4,5-trimethoxybenzaldehyde (829 mg, 4.23 mmol), p-toluenesulfonic acid monohydrate (2 mg), and anhydrous MgSO$_4$ in CH$_2$Cl$_2$ (15 ml) was stirred at room temperature for 11 days. The solids were removed by filtration and washed with fresh CH$_2$Cl$_2$. The filtrate was evaporated in vacuo and the residue was chromatographed over Woelm neutral alumina (2 cm column). Elution with 30% EtOAc in hexane followed by 3% CH$_3$OH in CH$_2$Cl$_2$ gave 155.5 mg (82%) of the title compound as a light yellow solid, mp 192°–196° C. (dec).

IR (KBr) 3445, 1776, 1585, 1490, 1460, 1380, 1330, 1235, 1128, 1038, 1005, 940, 760, 700 cm$^{-1}$.

$^1$H NMR (CDCl$_3$) δ 8.39 (s,1H), 7.11 (s,2H), 6.81 (s,1H), 6.53 (s,1H), 6.53–6.49 (m,2H), 5.97 (d,2H), 4.91 (d,1H), 4.73 (q,1H), 4.63 (d,1H), 4.59 (d,1H), 4.41 (dd,1H), 4.24–4.08 (m,2H), 3.91 (br s,9H), 3.80 (s,3H), 3.72 (dd,1H), 3.55 (dd,1H), 3.42 (dd,1H), 3.32–3.17 (m,3H), 2.94–2.88 (m,1H), 1.37 (d,3H).

EXAMPLE 22

3'-Desmethoxy-3'-[[(3-nitro)phenyl]methylene]amino etoposide (VII; A=methyl; Y=R$^3$=H; R$^6$=3-nitrophenyl)

A solution of 3'-aminoetoposide Va (200 mg, 0.349 mmol) and m-nitrobenzaldehyde (83 mg, 0.55 mmol) in EtOH (10 ml) was treated with p-toluenesulfonic acid monohydrate (3 mg). After 15 minutes, the resultant precipitate was isolated by filtration and washed with cold CH$_3$OH to give 20 mg of a yellow crystalline solid. The filtrate was evaporated and crystallization of the residue gave 150 mg of the title compound as a yellow solid (combined yield 69%).

IR (KBr) 3445, 1775, 1605, 1535, 1505, 1485, 1355, 1235, 1095, 1075, 1040, 1005, 935, 890, 870 815, 735, 680 cm$^{-1}$.

Partial $^1$H NMR (d6-DMSO) δ 8.79 (s,1H), 8.39 (d,1H,J=7.5Hz), 8.34–8.30 (m,2H), 7.76 (dd,1H), 6.99 (s,1H), 6.65 (d,1H,J=1.3Hz), 6.53 (s,1H), 6.26 (d,1H,J=1.3Hz), 6.00 (s,2H), 5.25–5.22 (m,2H), 4.95 (d,1H), 4.73 (q,1H), 4.58 (d,1H), 4.52 (d,1H), 4.29–4.26 (m,2H), 4.07 (dd,1H), 3.72 (s,3H), 1.23 (d,3H,J=5Hz).

EXAMPLE 23

3'-Desmethoxy-3'-[(N,N-dimethylamino)methylene]amino etoposide (IX; A=R$^7$=R$^8$=methyl; Y=R$^3$=H)

To a solution of 3'-aminoetoposide Va (0.26 g, 0.454 mmol) stirring at 20° C. in CHCl$_3$ (4 ml) under N$_2$ was added N,N-dimethyl dimethylformamide acetal (80 1, 0.60 mmol). After 20 minutes, thin layer chromatography showed the presence of the product (TLC rf=0.18; 10% MeOH in CH$_2$Cl$_2$) and no starting material (TLC rf=0.25). The solvent was removed on high vacuum. Flash chromatography on silica gel using 80% EtOAc in hexane then EtOAc as eluent provided 171 mg of light brown solid which was rechromatographed on silica gel using 10% then 20% then 30% acetone in EtOAc to provide 85 mg (30%) of an off-white solid: mp. 198°–200° C.

IR (KBr) 3440 (b), 2925, 1780, 1645, 1615 cm$^{-1}$.

$^1$H NMR (CDCl$_3$) δ 7.60 (s,1H), 6.82 (s,1H), 6.57 (s,1H), 6.37 (s,1H), 6.17 (s,1H), 5.99 (d,J=4.4Hz,2H), 4.91 (d,J=3.4Hz,1H), 4.76 (q,J=9.0Hz,1H), 4.66 (d,J=2Hz,1H), 4.58 (d,J=4.6Hz,1H), 4.42 (t,J=9.6Hz,1H), 4.22 (t,J=7.8Hz,2H), 3.75 (s,3H), 3.60 (t,J=9Hz,1H), 3.49–3.21 (m,5H), 3.03 (s,6H), 2.95 (m,1H), 1.41 (d, J=6.0Hz,3H).

FAB MS m/e (relative intensity) 629 (MH+).

EXAMPLE 24

3'-Desmethoxy-3'-nitro etoposide (XII; A=methyl; Y=R$^3$=H)

A solution of 3'-aminoetoposide Va (100 mg, 0.174 mmol) in CH$_2$Cl$_2$ (5 ml) was treated over 3 minutes with solid m-CPBA (Aldrich 80-85%, 114 mg, 0.542 mmol) and stirred at room temperature for 6 days. The mixture was partitioned with saturated aqueous sodium bicarbonate (75 ml) and CH$_2$Cl$_2$ (75 ml). The aqueous portion was then diluted with pH 7 phosphate buffer (70 ml) and brine (50 ml) and further extracted with CH$_2$Cl$_2$ (20 ml) and EtOAc (100 ml). The organic layers were washed with brine, dried over Na$_2$SO$_4$, and concentrated in vacuo. The residue was flash chromatographed on silica gel using 2-5% CH$_3$OH in CH$_2$Cl$_2$ to provide 83.7 mg (82%) of the pure title compound.

IR (KBr) 3460, 1775, 1630, 1550, 1492, 1455, 1393, 1340, 1275, 1240, 1160, 1100, 1080, 1040, 935, 890, 760, 705 cm$^{-1}$.

$^1$H NMR (CDCl$_3$) δ 7.42 (d,1H,J=1.6Hz), 6.83 (s,1H), 6.76 (d,1H,J=1.6Hz), 6.44 (s,1H), 5.99 (d,2H), 4.93 (d,1H,J=3.2Hz), 4.72 (q,1H,J=5Hz), 4.62 (d,1H,J=7.6Hz), 4.59 (d,1H,J=5.4Hz), 4.42 (dd,1H), 4.23 (dd,1H), 4.15 (dd,1H), 3.94 (s,3H), 3.71 (dd,1H), 3.55 (m,1H), 3.41 (dd,1H), 3.37-3.27 (m,3H), 2.81-2.73 (m,1H), 1.37 (d,3H,J=5Hz).

$^{13}$C NMR (CDCl$_3$) δ 174.6, 149.3 149.1, 147.6, 145.6, 133.2, 131.0, (2C's), 128.5, 121.3, 116.3, 110.2, 109.2, 102.0, 101.7, 99.7, 79.6, 73.5, 73.0, 68.0, 67.9, 66.4, 56.7, 43.0, 40.7, 37.3, 20.1.

EXAMPLE 25

3'-Desmethoxy-3'-diazonium etoposide hydroxide inner salt (Xa; A=methyl; Y=H)

Glacial acetic acid (3.0 ml, 26.2 mmol) followed NaNO$_2$ (0.15 g, 2.17 mmol) were added to a solution of 3'-aminoetoposide Va (0.22 g, 0.384 mmol) in dry THF (17 ml) stirring at 0° C. under N$_2$. The reaction mixture was stirred for 3.4 hours at 0° C. and poured into 150 ml of CH$_2$Cl$_2$. The dark red organic layer was washed with 100 ml of aqueous NaHCO$_3$. The combined organic extracts were washed with 100 ml of saturated NaHCO$_3$, dried over MgSO$_4$ and concentrated in vacuo to provide 0.177 g (79%) of a reddish orange solid: mp. slow decomposition 150° C.

IR (KBr) 3440 (b), 2930, 2160, 2120, 1779 cm$^{-1}$.

$^1$H NMR (CDCl$_3$) δ 6.78 (s,1H), 6.53 (s,1H), 6.52 (s,1H), 5.97 (d,J=8.3Hz,2H), 5.82 (s,1H), 4.86 (d,J=2.2Hz,1H), 4.72 (m,1H), 4.54 (d,J=7.6Hz,1H), 4.43 (t,J=9.0Hz,1H), 4.35 (d,J=5.1Hz,1H), 4.26 (t,J=8.3Hz,1H), 4.14 (m,1H), 3.71 (s,3H), 3.55 (t,J=9.7Hz,1H), 3.3 (bm,4H), 3.02 (m,1H), 1.35 (d,J=4.9Hz,3H).

EXAMPLE 26

3'-Desmethoxy-3'-azido etoposide (XI; A=methyl; Y=R$^3$=H)

To a solution of 3'-aminoetoposide Va (210 mg, 0.366 mmol) in dry THF (10 ml) cooled to 0° C. under N$_2$ was added glacial acetic acid (2 ml) followed by solid sodium nitrite (149 mg, 2.16 mmol). The mixture was stirred at 0° C. for 2 hours and at room temperature for 1 hour. A solution of sodium azide (110 mg, 1.69 mmol) in H$_2$O (1 ml) was then added and after 15 minutes, an additional 200 mg of solid sodium azide was added. The mixture was stirred at room temperature for 30 minutes and then partitioned with CH$_2$Cl$_2$ (100 ml), saturated aqueous sodium bicarbonate (30 ml), and H$_2$O (100 ml). The aqueous portion was further extracted with CH$_2$Cl$_2$ (2×40 ml) and the combined organic portions were washed with H$_2$O (65 ml) and brine (75 ml), and dried over Na$_2$SO$_4$. Rotary evaporation followed by chromatography on E. Merek 230-400 mesh silica gel (0.45 g) using CH$_2$Cl$_2$ followed by 2% CH$_3$OH in CH$_2$Cl$_2$ as eluent produced 210 mg (96%) of the pure title compound as a golden yellow solid.

IR (KBr) 3460, 2120, 1775, 1612, 1510, 1490, 1240, 1165, 1080, 1045, 1006, 935, 700 cm$^{-1}$.

$^1$H NMR (CDCl$_3$) δ 6.80 (d,1H), 6.79 (s,1H), 6.48 (s,1H), 5.99 (ABq,2H), 5.79 (d,1H,J=1.6Hz), b 4.88 (d,1H,J=3.5Hz), 4.73 (q,1H,J=5Hz), 4.62 (d,1H,J=7.5 Hz), 4.54 (d,1H,J=5.3Hz), 4.38 (dd,1H), 4.23-4.15 (m,2H), 3.85 (s,3H), 3.74 (m,1H), 3.56 (m,1H), 3.41 (dd,1H), 3.33-3.30 (m,2), 3.24 (dd,1H), 2.89-2.83 (m,1H), 1.37 (d,3H,J=5Hz).

EXAMPLE 27

Etoposide benzoxazole derivative (VIII; A=methyl; Y=R$^{14}$=H)

A solution of 3'-aminoetoposide Va (240 mg, 0.419 mmol) in 9:1 CH$_2$Cl$_2$/CH$_3$OH was treated with trimethyl orthoformate (1 ml) and 1-2 drops of 60% perchloric acid. The mixture was stirred at room temperature for 18 hours, after which the solvent was removed in vacuo and the residue purified by preparative silica gel chromatography (9:1 CH$_2$Cl$_2$/CH$_3$OH) to give 80 mg (33%) of the title compound as a colorless solid.

$^1$H NMR (CDCl$_3$) δ 7.97 (s,1H), 7.18 (br s,1H), 6.81 (s,1H), 6.52 (br s,2H), 5.97 (m,2H), 4.90 (d,2H,J=3.4Hz), 4.75-4.71 (m,2H), 4.64 (d,1H,J=7.5Hz), 4.41 (dd,1H), 4.20-4.15 (m,2H), 4.02 (s,3H), 3.76-3.72 (m,1H), 3.58-3.54 (m,1H), 3.45-3.41 (m,1H), 3.37-3.32 (m,3H), 2.95-2.90 (m,1H), 1.37 (d,3H,J=5Hz).

EXAMPLE 28

5'-Desmethoxy-5'-acetylamino etoposide 3',4'-orthoquinone (XIV; A=methyl; R$^{11}$=acetyl; Y=H)

Acetic acid (1.5 ml, 26.2 mmol) followed by sodium nitrite (34 mg, 0.49 mmol) was added to a solution of 3'-acetamidoetoposide (0.150 g, 0.244 mmol) in 10 ml of dry THF stirring at 2° C. under N$_2$. The clear solution slowly turned red and gradually darkened as the reaction proceeded. The reaction mixture was stirred for 3.5 hours at 2° C., poured into 100 ml of 50% EtOAc in Et$_2$O, and washed with two 50 ml portions of saturated aqueous sodium bicarbonate and one 50 ml portion of saturated aqueous brine. The organic layer was dried over MgSO$_4$, concentrated in vacuo, and flash chromatographed on silica gel using 5% MeOH in CH$_2$Cl$_2$ as eluent to provide 91 mg (62%) of a dark red solid: mp. 245°-250° C., TLC rf (5% MeOH in CH$_2$Cl$_2$).

IR (KBr) 3450 (b), 2925, 1779, 1669 cm$^{-1}$.

$^1$H NMR (CDCl$_3$) δ 7.78 (m,2H), 6.77 (s,1H), 6.56 (s,1H), 5.99 (m,2H), 5.70 (s,1H), 4.89 (d,J=3.24Hz,1H), 4.74 (q,J=5.1Hz,1H), 4.56 (d,J=7.8Hz,1H), 4.45 (t,J=3.2Hz,1H), 4.34 (t,J=7.5Hz,1H), 4.26 (d,J=6.3Hz,1H), 4.16 (dd,J=4,2.1Hz,1H), 3.70 (t,J=8.5Hz,1H), 3.57 (m,1H), 3.42 (t,J=11.8Hz,2H), 3.34-3.29 (m,2H), 2.89 (m,1H), 2.75 (bs,1H), 2.50 (bs,1H), 1.37 (d,J=4.9Hz,3H).

EXAMPLE 29

5'-Desmethoxy-5'-[[(2-chloroethyl)amino]carbonyl]amino etoposide 3',4'-ortho-quinone (XIV; A=methyl; $R^{11}$=2[(chloroethyl)amino]carbonyl)

The general procedure described in Example 28 was followed using the produce of Example 10 in place of 3'-acetylamino etoposide to afford the title compound, mp. 195°–197° C. (decomp).

IR (KBr) 3400 (b), 2940, 1780 cm$^{-1}$.

$^1$H NMR (CDCl$_3$) δ 8.62 (s,1H), 7.53 (s,1H), 7.43 (s,1H), 7.28 (bt,J=7.2Hz,1H), 6.83 (s,1H), 6.61 (s,1H), 5.98 (bs,2H), 5.59 (s,1H), 4.95 (d,J=3.1Hz,1H), 4.79 (m,2H), 4.58–4.30 (m,3), 4.28–4.13 (m,2H), 3.80–3.60 (bm,7H), 3.60–3.25 (bm,3H), 2.98 (m,1H), 1.41 (d,J=5.1Hz,3H).

FAB MS m/e (relative intensity) 665 (MH+).

EXAMPLE 30

5'-Desmethoxy-5'-[[(2,2,2-trichlorethyloxy]carbonyl]amino etoposide 3',4'-ortho-quinone (XIV; A=methyl; $R^{11}$=2,2,2-[(trichloroethyl)oxy]carbonyl)

The general procedure described in Example 28 was followed using the product of Example 9 in place of 3'-acetylamino etoposide to afford the title compound.

EXAMPLES 31–33

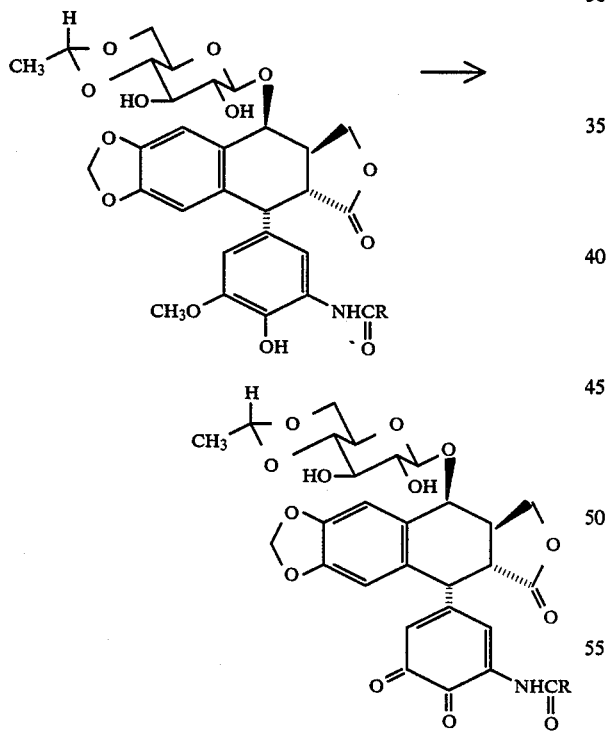

3'-acetylamino etoposide to provide the corresponding ortho-quinone derivatives.

| Example | Etoposide Reactant |
|---|---|
| 31 | R = H (Example 6) |
| 32 | R = CF$_3$ (Example 8) |
| 33 | R = —NHCH$_2$Ph (Example 11) |

EXAMPLE 34

3'-Desmethoxy-5'-demethyl-3'-acetylamino etoposide (XV; A=methyl; Y=H; $R^{11}$=acetyl)

The procedure of Example 7 was followed using 65.4 μl (0.69 mmol) of acetic anhydride and 0.38 g (0.66 mmol) of 3'-aminoetoposide Va in 10 ml of CH$_2$Cl$_2$. The product obtained after drying over MgSO$_4$ and concentration in vacuo was dissolved in 10 ml of anhydrous THF and reacted with 1.5 ml (26.2 mmol) of acetic acid followed by 0.182 g (2.64 mmol) of sodium nitrite in accordance to the procedure described in Example 30. The dark red solid obtained after flash chromatography was dissolved in 100 ml of EtOAc. Saturated aqueous sodium metabisulfite (60 ml) was added and the mixture shaken (less than one minute) until the dark red color disappeared leaving a faintly pink organic layer which was dried over MgSO$_4$ and concentrated in vacuo. Flash chromatography on silica gel using 4% MeOH in CH$_2$Cl$_2$ provided 73 mg (18%) of the product as a tan solid; mp. 210°–220° C. (decomp.)

IR (KBr) 3440 (b), 2945, 1775 cm$^{-1}$.

IR (Kbr) 3440 (b), 2945, 1775 cm$^{-1}$.

$^1$H NMR (CDCl$_3$) δ 9.49 (bs,2H), 6.97 (bs,2H), 6.84 (s,1H), 6.61 (d,J=2.0Hz,1H), 6.46 (s,1H), 6.20 (d,J=2.0Hz,1H), 5.95 (s,2h), 4.94 (d,J=3.6Hz,1H), 4.75 (q,J=5.2Hz,1h), 4.55–4.39 (m,3H), 4.30–4.16 (m,2H), 3.61 (m,2H), 3.43–3.29 (m,4H), 2.98 (bm,1H), 2.19 (s,3H), 1.38 (d,J=4.8Hz,3H).

FAB MS (m/e) 602 (MH+).

EXAMPLES 35–38

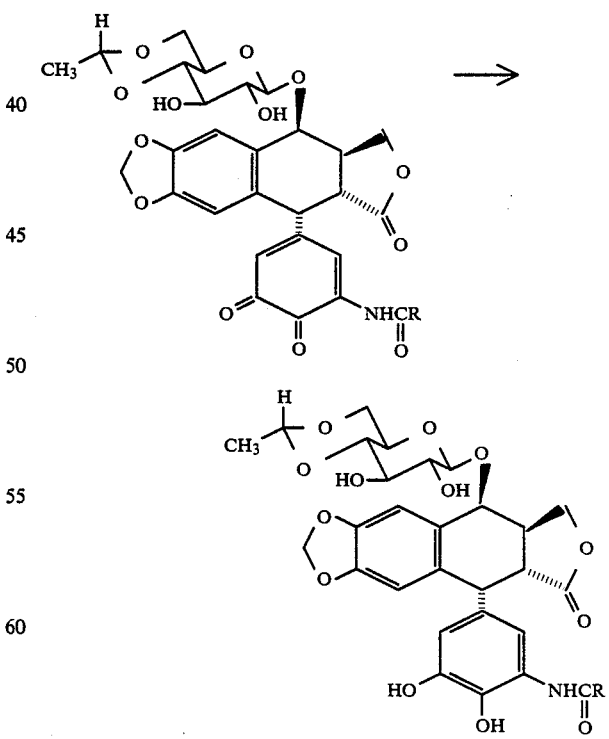

Reduction using sodium metabisulfite as described in Example 34 is applied to the following ortho-quinones to provide the corresponding hydroquinones.

| Example | R |
|---|---|
| 35 | NHCH$_2$CH$_2$Cl (Example 29) |
| 36 | H (Example 31) |
| 38 | —NHCH$_2$Ph (Example 33) |

EXAMPLE 39

3'-Desmethoxy-5'-demethyl-3'-[[(2,2,2-trichloro)ethyl]oxy]carbonyl]amino etoposide (XV; A=methyl; Y=H; R$^{11}$=2,2,2-trichloro)ethyl]oxycarbonyl)

Sodium nitrite (0.200 g, 2.90 mmol) was added to a solution of etoposide 5'-trichloroethylcarbamate (product of Example 11, 0.354 g, 0.473 mmol) and acetic acid (3 ml) in THF (10 ml) stirring at 2° C. under N$_2$. The reaction mixture was stirred for 3 hours and the red solution was poured into saturated aqueous NaHCO$_3$ (80 ml) and extracted with 80 ml of EtOAc and then two 25 ml portions of EtOAc. The combined organic layers were washed with aqueous NaCl (50 ml), dried over Na$_2$SO$_4$ and concentrated in vacuo to provide a red solid which was dissolved in 7 ml of THF. H$_2$O (1 ml) and glacial AcOH (1 ml) were added. The reaction mixture was cooled in an ice water bath and activated zinc (0.20 g, 3.06 mmol) was added thereto. The reaction mixture was removed from the ice bath. The red color faded quickly and after 15 minutes the reaction was poured into water and extracted three times with EtOAc. The organic layers were dried over MgSO$_4$ and purified by flash chromatography on silica gel using 5% MeOH in CH$_2$Cl$_2$ as eluent to provide 0.2052 g (58%) of an off-white solid.

IR (KBr) 3440, 2930, 1772 (b), 1623 cm$^{-1}$.

$^1$H NMR (CDCl$_3$) δ 8.12 (bs,1H), 7.79 (bs,1H), 7.64 (bs,1H), 6.73 (s,1H), 6.64 (s,1H), 6.26 (s,1H), 6.24 (s,1H), 5.73 (m,2H), 4.75 (d,J=3.4Hz,1H), 4.76–4.43 (m,4H), 4.31 (d,J=7.5Hz,1H), 4.24–4.15 (m,2H), 4.02–3.95 (m,2H), 3.43–3.33 (m,2H), 3.20–3.05 (m,2H), 2.86–2.78 (m,1H), 1.16 (d,J=5.0Hz,3H).

MS (FAB) m/e 734 (M+H)$^{30}$.

EXAMPLE 40

3'-Desmethoxy-5'-demethyl-3'-amino etoposide (XVI; A=methyl; Y=H)

Activated zinc dust (0.40 g, 6.11 mmol) was added to a solution of etoposide dihydroxy trichlorethylcarbamate (0.205 g, 0.273 mmol) in 5 ml THF, 0.5 ml H$_2$O, and 0.5 ml glacial AcOH stirring at room temperature. The reaction vessel was suspended in a sonicator for 90 minutes TLC analysis (5% MeOH in CH$_2$Cl$_2$ on silica gel) showed the formation of a product of lower rf than the starting material. The reaction was poured into water and extracted four times with EtOAc. The combined organic extracts were dried over Na$_2$SO$_4$, concentrated, and purified by flash chromatography on silica gel using 5% MeOH in CH$_2$Cl$_2$ as eluent, to provide 29 mg (19%) of dark grey metallic solid.

IR (KBr) 3434, 2923, 1767, 1734, 1486 cm$^{-1}$.

$^1$H NMR (CDCl$_3$/DMSO) δ 7.75 (bs,1H), 6.61 (s,1H), 6.26 (s,1H), 5.76 (s,1H), 5.71 (m,2H), 5.67 (s,1H), 4.70 (d,J=3.2Hz,1H), 4.53 (m,1H), 4.45 (bs,1H), 4.28 (d,J=7.7Hz,1H), 4.22–4.13 (m,2H), 3.966 (m,2H), 3.50 (bm,1H), 3.34 (m,2H), 3.15–3.0 (m,3H), 2.80–2.75 (m,1H), 1.15 (d,J=4.9Hz,3H).

MS (FAB) m/e 560 (M+H)$^+$.

EXAMPLE 41

3'-desmethoxy-3'-methyltriaenyl etoposide (XIII; A=R$^9$=methyl; Y=R$^3$=H)

The product of Example 9 in CH$_2$Cl$_2$ is treated with pyridine followed by 2-trimethylsilylethoxy methylchloride to provide silylethoxymethylacetal phenol protected derivative. Activated zinc dust is added to a solution of the phenol protected compound in THF/H$_2$O/ACOH. The 3'-amino product thus obtained is diazotized with HCl/NaNO$_2$. Reaction of the diazonium compound with methylamine and subsequent removal of the SEM ether protecting group using Bu$_4$NF provides the title compound.

EXAMPLE 42

3'-desmethoxy-3'-amino etoposide ortho-quinone (XIX; A=methyl; Y=H)

The product of Example 40 is diazotized and then treated with sodium azide, following the general procedure described in Example 26. Refluxing the resultant azido compound in chloroform affords the title compound.

What is claimed is:

1. A compound having the formula

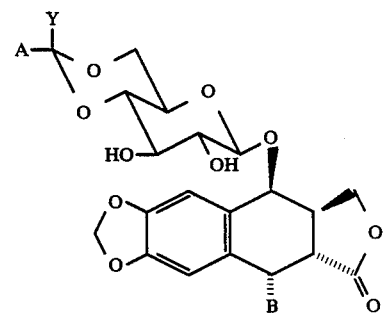

Y is H and A is selected from the group consisting of (C$_{1-10}$)alkyl; (C$_{2-20}$)alkenyl; (C$_{5-6}$)cycloalkyl; 2-furyl; 2-thienyl; aryl, aralkyl, and aralkenyl, each of the aromatic rings may be unsubstituted or substituted with one or more groups selected from halo, (C$_{1-8}$)alkyl, (C$_{1-8}$)alkoxy, hydroxy, nitro, and amino; or A and Y are each (C$_{1-8}$)alkyl; or A, Y, and the carbon to which they are attached join to form a (C$_{5-6}$) cycloalkyl group; and B is selected from the group consisting of

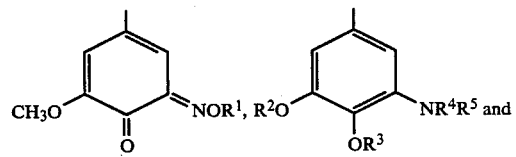

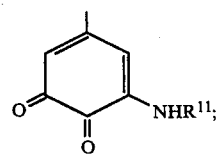

wherein R¹ is $(C_{1-10})$alkyl, $(C_{4-7})$cycloalkyl, $(C_{2-10})$alkenyl, $(C_{2-10})$alkynyl, each of the above groups may be unsubstituted or substituted with one or more Z; aryl, heteroaryl, aralkyl, or heteroaralkyl, the ring portion of the above groups may be unsubstituted or substituted with one or more groups selected from $(C_{1-8})$alkyl and Z; wherein said Z is selected from halo, $(C_{1-5})$alkoxy, amino, nitro, cyano, hydroxy, and mercapto;

R² is H or methyl;

R¹¹ is H, $$-\underset{\underset{O}{\|}}{C}H, \quad -\underset{\underset{O}{\|}}{C}R^{10}, \quad -\underset{\underset{O}{\|}}{C}OR^{10}, \text{ or } -\underset{\underset{O}{\|}}{C}NHR^{10}$$

wherein R¹⁰ is aryl$(C_{1-5})$alkyl, or $(C_{1-10})$alkyl unsubstituted or substituted with one or more Z;

R³ is H or a phenol protecting group;

R⁴ and R⁵ are each independently selected from $(C_{1-10})$alkyl, $(C_{4-7})$cycloalkyl, $(C_{2-10})$alkenyl, $(C_{2-10})$alkynyl, each of the above groups may be unsubstituted or substituted with one or more Z; aryl, heteroaryl, aralkyl, heteroaralkyl, the ring portion of the above groups may be unsubstituted or substituted with one or more groups selected from $(C_{1-8})$alkyl and Z; H, $$-\underset{\underset{O}{\|}}{C}H, \quad -\underset{\underset{O}{\|}}{C}-OR^{10}, \quad -\underset{\underset{O}{\|}}{C}R^{10} \text{ and } -\underset{\underset{O}{\|}}{C}-NHR^{10};$$

wherein Z and R¹⁰ are as defined above; or

R⁴ is H and R⁵ is selected from the group consisting of sulfonyl, wherein R¹² is H or $(C_{1-8})$alkyl; R¹³ is selected from the group consisting of H, a group within the definition for R¹, and —SR¹ wherein R¹ is as defined above; or R³, R⁴ and R⁵ together is —CR¹⁴= wherein R¹⁴ is H or $(C_{1-5})$alkyl; or NR⁴R⁵ taken together is selected from the group consisting of nitro, azido, N=CHR⁶, N=CHNR⁷R⁸, and N=NNHR⁹ wherein R⁶ is a group within the definition for R¹; R⁷ and R⁸ are each independently H or $(C_{1-8})$alkyl; R⁹ is $(C_{1-8})$alkyl; or NR⁴R⁵ taken together is $N_2^{\oplus}X^{\ominus}$ wherein $X^{\ominus}$ is an anionic group with the proviso that R³ is not H; or R³ and NR⁴R⁵ together represent diazonium hydroxide inner salt.

2. The compound of claim 1 wherein B is wherein R¹ is $(C_{1-10})$alkyl, phenyl$(C_{1-10})$alkyl, or phenyl$(C_{1-10})$alkyl with the aromatic ring substituted with one or more groups selected from Z and $(C_{1-8})$alkyl wherein Z is as defined in claim 1.

3. The compound of claim 2 wherein Y is H and A is methyl or 2-thienyl.

4. The compound of claim 3 wherein A is methyl.

5. The compound of claim 4 wherein R¹ is $(C_{1-5})$alkyl.

6. The compound of claim 5 wherein R¹ is methyl.

7. The compound of claim 4 wherein R¹ is phenylmethyl.

8. The compound of claim 1 wherein B is wherein

R² is H or methyl;

R³ is H or a phenol-protecting group;

R⁴ is H and R⁵ is selected from the group consisting of sulfonyl, H, $$-\underset{\underset{O}{\|}}{C}H, \quad -\underset{\underset{O}{\|}}{C}R^{10}, \quad -\underset{\underset{O}{\|}}{C}OR^{10}, \quad -\underset{\underset{O}{\|}}{C}-NHR^{10},$$

$(C_{1-10})$alkyl, wherein R¹⁰ is as defined in claim 1; R¹² is H; R¹³ is H, $(C_{1-10})$alkyl, or —S—R¹, wherein R¹ is as defined in claim 1; or R⁴R⁵ are each $(C_{1-10})$alkyl; or R³, R⁴, R⁵ together is —CR¹⁴= wherein R¹⁴ is H or $(C_{1-5})$alkyl; or NR⁴R⁵ taken together is selected from the group consisting of nitro, azido, N=CHR⁶, N=CHNR⁷R⁸, N=NNHR⁹; wherein R⁶ is aryl, heteroaryl, the ring portion of each group may be unsubstituted or substituted with one or more groups selected from Z and $(C_{1-8})$ alkyl wherein Z is as defined in claim 1; R⁷ and R⁸ are each independently H or $(C_{1-8})$alkyl; R⁹ is $(C_{1-8})$alkyl; or NR⁴R⁵ taken together is $N_2^{\oplus}X^{\ominus}$ wherein $X^{\ominus}$ is an aninonic group with the proviso that R³ is not H; or R³ and NR⁴R⁵ is represent diazonium hydroxide inner salt.

9. The compound of claim 8 wherein Y is H and A is methyl or 2-thienyl.

10. The compound of claim 9 wherein A is methyl.

11. The compound of claim 10 wherein $R^2$ is methyl; $R^3$ and $R^4$ are each H.

12. The compound of claim 11 wherein $R^5$ is selected from the group consisting of H,

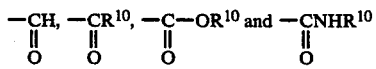

wherein $R^{10}$ is aryl $(C_{1-5})$alkyl or $(C_{1-10})$alkyl unsubstituted or substituted with one or more Z; wherein said Z is selected from halo, $(C_{1-5})$ alkoxy, amino, nitro, cyano, hydroxy, and mercapto.

13. The compound of claim 12 wherein $R^5$ is H.
14. The compound of claim 12 wherein $R^5$ is formyl.
15. The compound of claim 12 wherein $R^5$ is acetyl.
16. The compound of claim 12 wherein $R^5$ is trifluoroacetyl.
17. The compound of claim 12 wherein $R^5$ is 2,2,2-trichloroethoxycarbonyl.
18. The compound of claim 12 wherein $R^5$ is 2-chloroethylaminocarbonyl.
19. The compound of claim 12 wherein $R^5$ is phenylmethylaminocarbonyl.
20. The compound of claim 11 wherein $R^5$ is N-maleimide methyl.
21. The compound of claim 11 wherein $R^5$ is

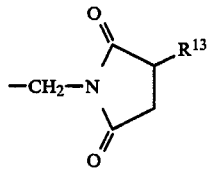

wherein $R^{13}$ is H, or —S—$R^1$ wherein $R^1$ is aryl$(C_{1-5})$alkyl or $(C_{1-10})$alkyl unsubstituted or substituted with one or more Z; wherein said Z is selected from halo, $(C_{1-5})$ alkoxy, amino, nitro, cyano, hydroxy, and mercapto.

22. The compound of claim 21 wherein $R^{13}$ is H.
23. The compound of claim 21 wherein $R^{13}$ is octylthio.
24. The compound of claim 21 wherein $R^{13}$ is 2-pyridylthio.
25. The compound of claim 11 wherein $R^5$ is sulfonyl.
26. The compound of claim 25 wherein $R^5$ is methanesulfonyl.
27. The compound of claim 11 wherein $R^5$ is $(C_{1-8})$alkyl.
28. The compound of claim 27 wherein $R^5$ is methyl.
29. The compound of claim 27 wherein $R^5$ is n-butyl.
30. The compound of claim 10 wherein $R^2$ is methyl; $R^3$ is H; and $NR^4R^5$ is $N=CHR^6$ wherein $R^6$ is as defined in claim 8.
31. The compound of claim 30 wherein $R^6$ is 2-furyl.
32. The compound of claim 30 wherein $R^6$ is 2-thienyl.
33. The compound of claim 30 wherein $R^6$ is 3,4,5-trimethoxyphenyl.
34. The compound of claim 30 wherein $R^6$ is 4-methoxyphenyl.
35. The compound of claim 30 wherein $R^6$ is 3-nitrophenyl.

36. The compound of claim 30 wherein $R^6$ is 4-pyridyl.
37. The compound of claim 10 wherein $R^2$ is methyl; $R^3$ is H; and $NR^4R^5$ is nitro.
38. The compound of claim 10 wherein $R^2$ is methyl; $R^3$ is H; and $NR^4R^5$ is azido.
39. The compound of claim 10 wherein $R^2$ is methyl; $R^3$ is a phenol-protecting group. and $NR^4R^5$ is $N_2^{\oplus}X^{\ominus}$ wherein $X^{\ominus}$ is an anionic group.
40. The compound of claim 10 wherein $R^2$ is methyl; $R^3$ is H; and $NR^4R^5$ is N,N-dimethylformamidine.
41. The compound of claim 10 wherein $R^2$ is methyl; $R^3$ is H; and $NR^4R^5$ is $N=NNHR^9$ wherein $R^9$ is $(C_{1-5})$alkyl.
42. The compound of claim 10 wherein $R^2$ is methyl; $R^3$ and $NR^4R^5$ represent diazonium hydroxide inner salt.
43. The compound of claim 10 wherein $R^2$ is methyl, $R^3$, $R^4$ and $R^5$ together is —CH=.
44. The compound of claim 10 wherein $R^2$, $R^3$, $R^4$ are each H; $R^5$ is selected from the group consisting of H,

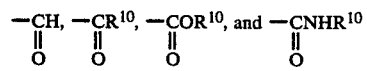

wherein $R^{10}$ is aryl $(C_{1-5})$alkyl or $(C_{1-10})$alkyl unsubstituted or substituted with one or more Z; wherein said Z is selected from halo, $(C_{1-5})$ alkoxy, amino, nitro, cyano, hydroxy, and mercapto.

45. The compound of claim 44 wherein $R^5$ is H.
46. The compound of claim 44 wherein $R^5$ is

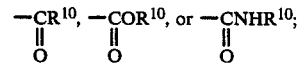

wherein $R^{10}$ is aryl $(C_{1-5})$ alkyl or $(C_{1-10})$alkyl unsubstituted or substituted with one or more Z; wherein said Z is selected from halo, $(C_{1-5})$ alkoxy, amino, nitro, cyano, hydroxy, and mercapto.

47. The compound of claim 46 wherein $R^5$ is acetyl.
48. The compound of claim 46 wherein $R^5$ is 2,2,2-trichloroethoxycarbonyl.
49. The compound of claim 10 wherein $R^2$, $R^3$ are each H; $NR^4R^5$ is azido.
50. The compound of claim 10 wherein $R^2$ is H; $R^3$ and $NR^4R^5$ represent diazonium hydroxide inner salt.
51. The compound of claim 10 wherein $R^2$ is H; $R^3$ is a phenol-protecting group; and $NR^4R^5$ is $N_2^{\oplus}X^{\ominus}$ wherein $X^{63}$ is an anionic group.
52. The compound of claim 1 wherein B is

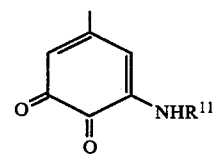

wherein
$R^{11}$ is H,

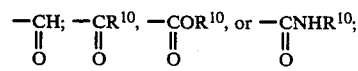

wherein $R^{10}$ is as defined in claim 1.

53. The compound of claim 52 wherein Y is H and A is methyl or 2-thienyl.

54. The compound of claim 53 wherein A is methyl.

55. The compound of claim 54 wherein $R^{11}$ is $$-\underset{\underset{O}{\|}}{C}R^{10}, -\underset{\underset{O}{\|}}{C}OR^{10}, \text{ or } -\underset{\underset{O}{\|}}{C}NHR^{10};$$

wherein $R^{10}$ is $(C_{1-10})$alkyl unsubstituted or substituted with one or more halo, or ara$_{(1-5)}$alkyl.

56. The compound of claim 55 wherein $R^{11}$ is acetyl.

57. The compound of claim 55 wherein $R^{11}$ is 2,2,2-trichloroethoxycarbonyl.

58. The compound of claim 55 wherein $R^{11}$ is 2-chloroethylaminocarbonyl.

59. The compound of claim 52 wherein $R^{11}$ is H.

* * * * *